(12) United States Patent
Hayashi et al.

(10) Patent No.: US 7,279,601 B2
(45) Date of Patent: Oct. 9, 2007

(54) OPTICALLY ACTIVE α-AMINOOXYKETONE DERIVATIVES AND PROCESS FOR PRODUCTION THEREOF

(75) Inventors: Yujiro Hayashi, Tokyo (JP); Mitsuru Shoji, Tokyo (JP)

(73) Assignee: Tokyo University of Science, Center for Science and Technology Exchange, Tokyo (JP)

( * ) Notice: Subject to any disclaimer, the term of this patent is extended or adjusted under 35 U.S.C. 154(b) by 0 days.

(21) Appl. No.: 10/569,757

(22) PCT Filed: Aug. 20, 2004

(86) PCT No.: PCT/JP2004/012008

§ 371 (c)(1),
(2), (4) Date: Feb. 24, 2006

(87) PCT Pub. No.: WO2005/019159

PCT Pub. Date: Mar. 3, 2005

(65) Prior Publication Data

US 2006/0293525 A1      Dec. 28, 2006

(30) Foreign Application Priority Data

Aug. 25, 2003 (JP) ............................ 2003-300367
May 24, 2004 (JP) ............................ 2004-153944

(51) Int. Cl.
C07C 239/00   (2006.01)
C07C 259/00   (2006.01)

(52) U.S. Cl. ................................. 564/300
(58) Field of Classification Search ............ 564/298
See application file for complete search history.

(56) References Cited

OTHER PUBLICATIONS

Brown et al (J. Am. Chem. Soc., 2003, 125, 10808-10809).*
Brown, Sean P., et al., *The Direct and Enantioselective Organocatalytic α-Oxidation of Aldehydes*, J.Am. Chem. Soc., vol. 125, No. 36, 2003, 10808-10809.
Ohtake, Hiroaki, et al., *Regioselective Synthesis of Nitrones by Decarboxylative Oxidation of N-Alkyl-α-amino Acids and Application to the Synthesis of 1-Azabicyclic Alkaloids*, Bull. Chem. Soc., Jpn., 72, No. 12 (1999) 2737-2754.
Momiyama, Norie, et al., *Catalytic Enantioselective Synthesis of α-Aminoaxy and α-Hydroxy Ketone Using Nitrosobenzene*, J. Am. Chem. Soc., vol. 125, No. 20, 2003, 6038-6039.
Zhong, Guofu, *A Facile and Rapid Route to Highly Enantiopure 1,2-Diols by Novel Catalytic Asymmetric α-Aminoxylation of Aldehydes*, Angew. Chem. Int. Ed. 2003, 42, 4247-4250.
Hayaski, Yujiro, et al., *Direct Proline Catalyzed Asymmetric α-Aminooxylation of Aldehydes*, Tetrahedron Letters 44 (2003) 8293-8296.
Davis, Franklin, et al., *Asymmetric Hydroxylation of Enolates with N-Sulfonyloxaziridines*, Chem. Rev. 1992, 92, 919-934.
Davis, Franklin, et al., *Stereochemistry of the Asymmetric Oxidation of Ketone Enolates Using (Camphorylsulfonyl) oxaziridines*, J. Org. Chem. 1986, 51, 4083-4085.
Chen, Bang-Chi, et al., *Enantioselective Synthesis of (+) -Kjellmanianone*, Tetrahedron vol. 47, No. 2, 173-182, 1991.
Davis, Franklin, et al., *Kinetic Resolution in the Asymmetric Hydroxylation of Enolates. Stereospecific Synthesis of (2S,3R)-(-)-Verrucarinolactone*, J. Org. Chem., 1992, 57, 3337-3339.
Davis, Franklin, et al., *Chemistry of Oxaziridines. 18. Synthesis and Enantioselective Oxidations of the [(8,8-Dihalocamphoryl)sulfonyl]oxaziridines$^{1,2}$* J. Org. Chem. 1992, 57, 7274-7285.
Davis, Franklin, et al., *Hydroxylation of Dihydroisoxazoles Using N-Sulfonyloxaziridines*, J. Org. Chem. 1993, 58, 7591-7593.
Davis, Franklin, et al., *Asymmetric Synthesis of the AB Ring Segments of Daunomycin and 4-Demethoxydaunomycin*, J. Org. Chem. 1994, 59, 1184-1190.
Morikawa, Kouhei, et al., *Catalytic Asymmetric Dihydroxylation of Tetrasubstituted Olefins*, J. Am. Chem. Soc. 1993, 115, 8463-8464.
Hashiyama, Tomiki, et al., *α-Hydroxy Ketones in High Enantiomeric Purity from Asymmetric Dihydroxylation of Enol Ethers*, J. Org. Chem. 1992, 57, 5067-5068.

(Continued)

*Primary Examiner*—Porfirio Nazario
*Assistant Examiner*—Kellette Gale
(74) *Attorney, Agent, or Firm*—Todd Deveau; Thomas, Kayden, Horstemeyer & Risley LLP

(57) ABSTRACT

The corresponding α-aminooxy ketone is manufactured with a high yield and a high enantioselectivity. A manufacturing method for an optically active α-aminooxy ketone derivative expressed by formula (1), wherein a ketone expressed by formula (2) is caused to react with a nitroso compound expressed by formula (3) in the presence of a proline derivative expressed by formula (4).

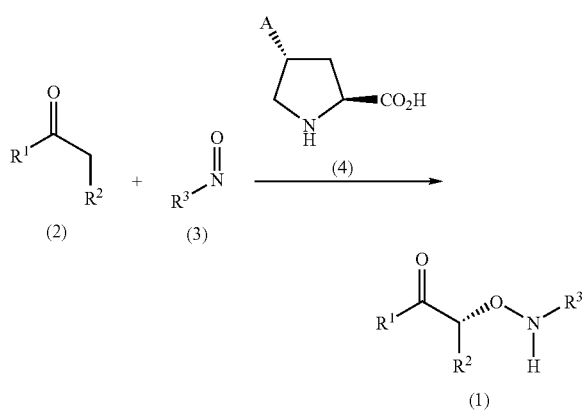

In the formula, $R^1$ and $R^2$ respectively denote an alkyl, alkenyl or alkynyl group, and $R^1$ and $R^2$ may be linked to form a ring. $R^3$ denotes an aryl, heterocyclic, alkyl, alkenyl or alkynyl group. A denotes a hydrogen atom, alkoxy group, aryloxy group, acyloxy group or silyloxy group which may have a substituent.

2 Claims, No Drawings

OTHER PUBLICATIONS

Fukuda, Tsutomu, et al., *Mn-Salen Catalyzed Asymmetric Oxidation of Enol Derivatives*, Tetrahedron Letters, vol. 37, No. 25, 4389-4392, 1996.

Adam, Waldemar, et al., *Synthesis of Optically Active α-Hydroxy Carbonyl Compounds by the Catalytic, Enantioselective Oxidation of Silyl Enol Ethers and Ketene Acetals with (Salen)manganese (III) Complexes*, J. Am. Chem. Soc. 1998, 120, 708-714.

Zhu, Yuanming, et al., *High Enantioselective Epoxidation of Enol Silyl Ethers and Esters*, Tetrahedron Letters 39 (1998) 7819-7822.

Adam, Waldemar, et al., *Synthesis of optically active α-hydroxy ketones by enantioselective oxidation of silyl enol ethers with a fructose-derived dioxirane*, Tetrahedron: Asymmetry 9 (1998) 397-401.

Hayashi, et al., "Direct Proline-Catalyzed Asymmetric Alpha-Aminoxylation of Ketones", Angew. Chem. Int. Ed. 2004, 43, pp. 1112-1115.

Bogevig, et al., "Direct Catalytic Enantioselective Synthesis Alpha-Aminoxylation of Keytones: A Stereoselective Synthesis of Alpha-Hydroxy and Alpha, Alpha'-Dihydroxy Ketones", Angew. Chem. Int. Ed. 2004, pp. 1109-1112.

Cordova, et al., "The Direct Catalytic Asymmetric Alpha-Aminooxylation Reaction: Development of Stereoselective Routes to 1,2-Diols and 1,2-Amino Alcohols and Density Functional Calculations", Chem. Eur. J. 2004, 10, pp. 3673-3684.

\* cited by examiner

OPTICALLY ACTIVE α-AMINOOXYKETONE DERIVATIVES AND PROCESS FOR PRODUCTION THEREOF

RELATED APPLICATION

This application claims priority to and the benefit of Japanese Patent Application No. 2003-300367 filed Aug. 25, 2003 and Japanese Patent Application No. 2004-153944 filed May 24, 2004.

TECHNICAL FIELD

The present invention relates to an α-aminooxy ketone derivative which can be easily converted into an α-hydroxy ketone useful for medicines, agricultural chemicals, and the like, and a manufacturing method by which the α-aminooxy ketone derivative can be obtained in a high yield with a high enantioselectivity.

BACKGROUND ART

Conventionally, an α-hydroxy ketone has been synthesized by first converting a ketone into an enolate or an equivalent thereof once, and then causing a diastereoselective reaction or an enantioselective reaction (see non-patent literature 1).

As an example of such a method, the method which converts a ketone into a lithium enolate, and causes optically active oxadilysine as an oxidizer to act thereon as an oxidizer (see patent literatures 2 to 8); the method which, as an asymmetric catalytic reaction, converts a ketone into an enol ether, and then carries out asymmetric dihydroxylation thereof (see non-patent literatures 9 to 10); and the technique which further carries out asymmetric epoxidation thereof (non-patent literatures 10 to 14), are known.

As described above, with these methods, it is necessary to first convert a ketone into the corresponding enolate or an equivalent thereof, and the catalytic asymmetric oxidation reaction has presented the problem that substrates with which a high asymmetric yield can be achieved are limited. Further, there has been another problem in that the asymmetric catalytic reaction requires use of an environmentally harmful metallic salt.

Recently, a method for synthesizing an α-aminooxy ketone by converting a ketone into a tin enolate, and then carrying out an asymmetric catalyzed reaction using nitrosobenzene using a catalytic amount of an optically active activating agent has been reported (non-patent literature 15).

The α-aminooxy ketone can be easily converted into an α-hydroxy ketone, thus this technique provides a part of a useful α-hydroxy ketone synthesizing method.

However, although this method requires a smaller amount of optically active catalyst, it has presented problems in that, for example, there is the need to first convert a ketone into a tin enolate; the tin compound has toxicity; and that the asymmetric catalyst used must be prepared from BINAP and AgOTf.

Thus, no excellent method for manufacturing an optically active α-hydroxy ketone directly from a ketone by an asymmetric catalytic reaction using an easily available asymmetric source as an activating agent has been provided. In addition, no manufacturing method which proceeds with high yield and asymmetric yield, meeting the requirements for practical use, has been available. In other words, no efficient manufacturing method from a ketone to an optically active α-hydroxy ketone has been provided.

Non-patent literature 1: Zhou et al. (Zhou, P.; Chen, B. C.; Davis, F. A. "Asymmetric Oxidation Reactions", Katsuki, T., Ed.; Oxford University Press: Oxford, 2001; p 128)

Non-patent literature 2: Davis et al. (Davis, F. A.; Chen, B. C. Chem. Rev. 1992, 92, 919)

Non-patent literature 3: Davis et al. (Davis, F. A.; Haque, M. S. J. Org. Chem. 1986, 51, 4083)

Non-patent literature 4: Chen et al. (Chen, B. C.; Weismiller, M. C.; Davis, F. A.; Boschelli, D.; Empfield, J. R.; Smith, A. B. Tetrahedron 1991, 47, 173)

Non-patent literature 5: Davis et al. (Davis, F. A.; Kumar, A. J. Org. Chem. 1992, 57, 3337)

Non-patent literature 6: Davis et al. (Davis, F. A.; Weismiller, M. C.; Murphy, C. K.; Reddy, R. T.; Chen, B. C. J. Org. Chem. 1992, 57, 7274)

Non-patent literature 7: Davis et al. (Davis, F. A.; Kumar, A.; Reddy, R. T.; Rajarathnam, E.; Chen, B. C.; Wade, P. A.; Shah, S. W. J. Org. Chem. 1993, 58, 7591)

Non-patent literature 8: Davis et al. (Davis, F. A.; Clark, C.; Kumar, A.; Chen, B. C. J. Org. Chem. 1994, 59, 1184)

Non-patent literature 9: Hashiyama et al. (Hashiyama, T.; Morikawa, K.; Sharpless, K. B. J. Am. Chem. Soc. 1993, 115, 8463)

Non-patent literature 10: Hashiyama et al. (Hashiyama, T.; Morikawa, K.; Sharpless, K. B. J. Org. Chem. 1992, 57, 5067)

Non-patent literature 11: Fukuda et al. (Fukuda, T.; Katsuki, T. Tetrahedron Lett. 1996, 37, 4389)

Non-patent literature 12: Adam et al. (Adam, W.; Rainer, T. F.; Stegmann, V. R.; Saha-Moller, C. R. J. Am. Chem. Soc. 1998, 120, 708)

Non-patent literature 13: Zhu et al. (Zhu, Y.; Yu, Y.; Yu, H.; Shi, Y. Tetrahedron Lett. 1998, 39, 7819)

Non-patent literature 14: Adam et al. (Adam, W.; Fell, R. T.; Saha-Moller, C. R.; Zhao, C-G Tetrahedron: Asymmetry 1998, 9, 397)

Non-patent literature 15: Momiyama et al. (Momiyama, N.; Yamamoto, H. J. Am. Chem. Soc., 2003, 125, 6038)

DISCLOSURE OF INVENTION

Problems to Be Solved by the Invention

Therefore, the purposes of the present invention are to provide a method for manufacturing, in a manner that is industrially advantageous, an optically active α-aminooxy ketone that is free from the above-mentioned problems and, in turn, to efficiently obtain an α-hydroxy ketone.

Means to Solve the Problems

In view of such circumstances, the present inventors have conducted intensive research, and have completed the present invention, finding that, by causing a ketone expressed by formula (2) to react with a nitroso compound expressed by formula (3) in the presence of proline or a specific proline derivative, an α-aminooxy ketone can be obtained in a high yield with a high enantioselectivity.

That is, the present invention provides:

<1> A manufacturing method for an optically active α-aminooxy ketone derivative expressed by formula (1), wherein a ketone expressed by formula (2) is caused to react with a nitroso compound expressed by formula (3) in the presence of proline or a proline derivative expressed by formula (4).

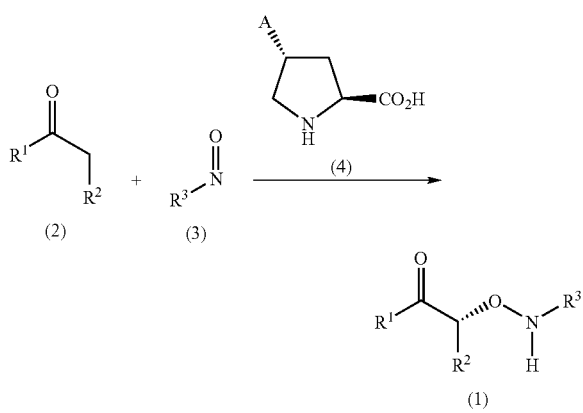

In formulae (1) to (4), $R^1$ and $R^2$ respectively denote an alkyl, alkenyl or alkynyl group which may have a substituent, and $R^1$ and $R^2$ may be linked to form a ring. $R^3$ denotes an aryl, heterocyclic, alkyl, alkenyl or alkynyl group which may have a substituent. A denotes a hydrogen atom, alkoxy group, aryloxy group, acyloxy group or silyloxy group which may have a substituent.

<2> The manufacturing method of item <1>, wherein A in formula (4) is a silyloxy group which may have a substituent.

<3> A manufacturing method for an optically active α-aminooxy ketone derivative expressed by formula (1'), wherein a ketone expressed by formula (2) is caused to react with a nitroso compound expressed by formula (3) in the presence of proline or a proline derivative expressed by formula (4').

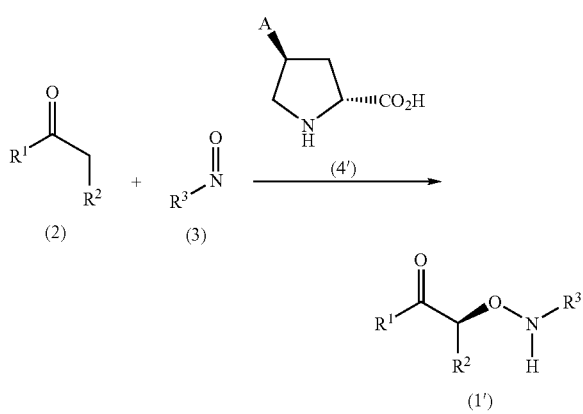

In formulae (1) to (4), $R^1$ and $R^2$ respectively denote an alkyl, alkenyl or alkynyl group which may have a substituent, and $R^1$ and $R^2$ may be linked to form a ring. $R^3$ denotes an aryl, heterocyclic, alkyl, alkenyl or alkynyl group which may have a substituent. A denotes a hydrogen atom, alkoxy group, aryloxy group, acyloxy group or silyloxy group which may have a substituent.

<4> The manufacturing method of item <3>, wherein A in formula (4') is a silyloxy group which may have a substituent.

<5> An optically active α-aminooxy ketone derivative or an enantiomer thereof which is expressed by formula (1a).

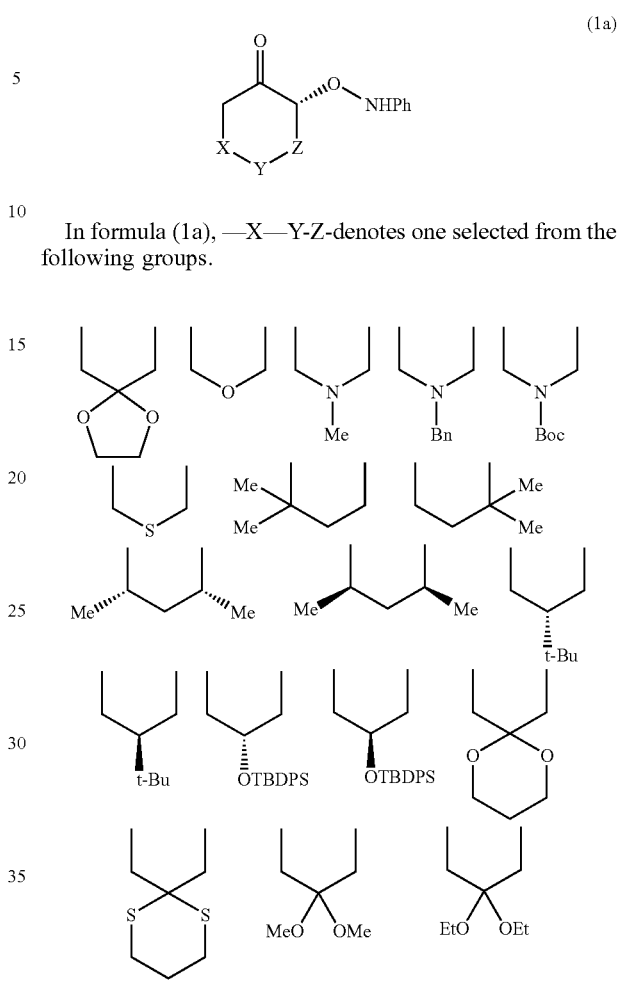

In formula (1a), —X—Y-Z-denotes one selected from the following groups.

Effects of the Invention

According to the present invention, an α-aminooxy ketone can be obtained in a high yield with a high enantioselectivity.

When the catalyst is proline, the proline has the feature of being inexpensive. When the catalyst used is a proline derivative and, in particular super proline as described below, the corresponding α-aminooxy ketone can be manufactured at a stroke simply in a short period of time with a high yield and a high enantioselectivity, as compared to proline.

Best Mode for Carrying Out the Invention

The manufacturing method for α-aminooxy ketones of the present invention provides a manufacturing method for an α-aminooxy ketone, wherein a ketone expressed by formula (2) as given above is caused to react with a nitroso compound expressed by formula (3) in the presence of proline or a proline derivative expressed by formula (4) or (4').

First, the raw material compounds will be described.

<Ketones Expressed by Formula (2)>

In formula (2), the alkyl group denoted by $R^1$ and $R^2$ preferably has 1 to 20 carbons, and particularly preferably has 1 to 5 carbons or so. Specific examples of the alkyl group include a methyl group, an ethyl group, propyl group, an isopropyl group, a n-butyl group, a sec-butyl group, a t-butyl group, a pentyl group, a hexyl group, a heptyl group, a n-octyl group, a 2-ethylhexyl group, a t-octyl group, a nonyl group, a decyl group, a dodecyl group, a tridecyl group, a tetradecyl group, a pentadecyl group, a n-hexadecyl group, a 2-hexyldecyl group, a heptadecyl group, an octadecyl group, a nonadecyl group, an icosyl group, and the like. The alkyl group may further have a substituent, and as such a substituent, the following aryl group, heterocyclic group, and the like can be mentioned.

Herein, examples of the aryl group include phenyl and naphthyl groups, which may have a substituent, and the like.

In addition, examples of the heterocycle in the heterocyclic group include piperidine, furan, thiophene, pyrrole, pyrazole, imidazole, triazole, oxazole, isooxazole, thiazole, isothiazole, dioxolane, pyridine, pyrimidine, pyrazine, triazine, dioxane, dithiane, morpholine, azepine, oxepine, thiepine, and the like.

The aryl group and the heterocyclic group may further have a substituent, and as such a substituent, an alkyl group, an alkenyl group, a nitro group, a halogen atom (for example, a fluorine atom, a chlorine atom, a bromine atom, or an iodine atom), and the like can be mentioned.

In formula (2), the alkenyl group denoted by $R^1$ and $R^2$ preferably has 2 to 20 carbons, and particularly preferably has 2 to 5 carbons or so. Specific examples of the alkenyl group include a vinyl group, a propenyl group, such as an allyl group, or the like, a butylyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, a octadecenyl group, a nonadecenyl group, an icosenyl group, and the like. The alkenyl group may further have a substituent, and as such a substituent, the above-mentioned aryl group, heterocyclic group, and the like can be mentioned.

The alkynyl group preferably has 2 to 20 carbons, and particularly preferably has 2 to 5 carbons.

In the ketone expressed by formula (2), $R^1$ and $R^2$ may be linked to form a ring. Examples of such a ring include cyclohexane, cyclopentane, cycloheptane, cyclooctane, cyclononane, tetrahydrofuran, tetrahydropyran, piperidine, pyrrolidine, thiacyclohexane, and the like. These rings may further have a substituent, and as such a substituent, the above-mentioned alkyl group, alkenyl group, alkynyl group, aryl group, heterocyclic group, and the like can be mentioned.

Specific examples of the ketone expressed by formula (2) include cyclohexanone, cyclopentanone, dimethylcyclohexanone, 1,4-cyclohexanedione, monoethyleneketal, tetrahydropyran-4-on, piperidinone, 3-pentanone, tetrahydrothiopyran-4-on, 3,3-dimethylcyclohexanone, cys-3,5-dimethylcyclohexanone, 3-methylcyclohexanone, 3-phenylcyclohexanone, 4-tert-butylcyclohexanone, 4-(tert-butyldiphenylsiloxy)cyclohexanone, cycloheptanone, 2-butanone, 1,5-dioxaspiro[5.5]undeca-9-on, 1,5-diaspiro[5.5]undeca-9-on, 4,4-dimethoxycyclohexanone, 4,4-diethoxycyclohexanone, and the like.

<Nitroso Compounds Expressed by Formula (3)>

In formula (3), as the aryl group denoted by $R^3$, phenyl and naphthyl groups, which may have a substituent, and the like can be mentioned, and the aryl group is preferably a phenyl group.

Examples of the heterocycle of the heterocyclic group denoted by $R^3$ in formula (3) include piperidine, furan, thiophene, pyrrole, pyrazole, imidazole, triazole, oxazole, isooxazole, thiazole, isothiazole, dioxolane, pyridine, pyrimidine, pyrazine, triazine, dioxane, dithiane, morpholine, azepine, oxepine, thiepine, and the like.

The aryl group and the heterocyclic group may further have a substituent, and as such a substituent, an alkyl group, an alkenyl group, a nitro group, a halogen atom (for example, a fluorine atom, a chlorine atom, a bromine atom, or an iodine atom), and the like can be mentioned.

In formula (3), the alkyl group denoted by $R^3$ preferably has 1 to 20 carbons, and particularly preferably has 1 to 5 carbons or so. Specific examples of the alkyl group include a methyl group, an ethyl group, a propyl group, an isopropyl group, a n-butyl group, a sec-butyl group, a t-butyl group, a pentyl group, a hexyl group, a heptyl group, a n-octyl group, a 2-ethylhexyl group, a t-octyl group, a nonyl group, a decyl group, a dodecyl group, a tridecyl group, a tetradecyl group, a pentadecyl group, a n-hexadecyl group, a 2-hexyldecyl group, a heptadecyl group, a octadecyl group, a nonadecyl group, an icosyl group, and the like. The alkyl group may further have a substituent, and as such a substituent, the above-mentioned aryl group, heterocyclic group, and the like can be mentioned.

In formula (3), the alkenyl group denoted by $R^3$ preferably has 2 to 20 carbons, and particularly preferably has 2 to 5 carbons or so. Specific examples of the alkenyl group include a vinyl group, propenyl group, such as an allyl group, or the like, a butylyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, and the like. The alkenyl group may further have a substituent, and as such a substituent, the above-mentioned aryl group, heterocyclic group, and the like can be mentioned.

The alkynyl group denoted by $R^3$ preferably has 2 to 20 carbons, and particularly preferably has 2 to 5 carbons.

The nitroso compound expressed by formula (3) is preferably nitrobenzene.

<Proline or Proline Derivatives Expressed by Formula (4) or (4')>

In the present invention, as the asymmetric catalyst, proline or a proline derivative expressed by formula (4) or (4') is used.

In formulae (4) and (4'), A denotes a hydrogen atom, alkoxy group, aryloxy group, acyloxy group or silyloxy group which may have a hydrogen atom. Herein, as the alkoxy group, those which have 1 to 5 carbons, for example, a methoxy group, an ethoxy group, a propoxy group, a butoxy group, a pentyloxy group, and the like can be mentioned. As the aryloxy group, a phenyloxy group, a naphthyloxy group, and the like can be mentioned. As the acyloxy group, an acetoxy group, a benzoyloxy group, and the like can be mentioned. As the substituent of the silyloxy group, an alkyl group, an aryl group, an alkenyl group, and the like can be mentioned. Those in which A is a methoxy group are described in the literature of Roda et al. (Roda, Aldo; Cerre, Carolina; Manetta, Anna C.; Cainelli, Gianfranco; Ronchi, Achille Umani; Panunzio, Mauro. Journal of Medicinal Chemistry (1996), 39 (11), 2270-6.), and those in which A is a benzoyloxy group are described in the literature of Perni et al. (Perni, Robert B.; Britt, Shawn D.; Court, John C.; Courtney, Lawrence F.; Deininger, David D.; Farmer, Luc J.; Gates, Cynthia A.; Harbeson, Scott L.; Kim, Joseph L.; Landro, James A.; Levin, Rhonda B.; Luong, Yu-Ping; O'Malley, Ethan T.; Pitlik, Janos; Rao, B. Govinda; Schairer, Wayne C.; Thomson, John A.; Tung, Roger D.; Van Drie, John H.; Wei, Yunyi. Bioorganic & Medicinal Chemistry Letters (2003), 13 (22), 4059-4063.).

A is preferably a tert-butyldimethylsilyloxy group or a triisopropylsilyloxy group, and particularly preferably a tert-butyldimethylsilyloxy group (the proline which has this group may be called "super proline") is preferable. The super proline causes the reaction to be completed in a much short period of time with the asymmetric yield being extremely high, as compared to the proline, in which A is a hydrogen atom. The super proline is public known (H. Ohtake, Y Imada, S-I. Murahashi, Bull. Chem. Soc. Jpn. 1999, 72, 2737.).

<Reaction Conditions>

First, by dissolving a ketone expressed by formula (2) as given above and proline or a proline derivative (4) [because, with (4'), the reaction progresses in the same way, herein (4) also means (4')] into an organic solvent, a solution is prepared. Herein, the proline or proline derivative (4) is preferably used in an amount of 0.01 to 1 equiv., and particularly in an amount of 0.1 to 0.3 equiv, relative to a nitroso compound (3). Herein, the organic solvent to be used is preferably a polar solvent, such as DMF, DMSO, $CH_3NO_2$, NMP (N-methyl-pyrrolydinone), $CH_3CN$, $CHCl_3$, $CH_2Cl_2$, or the like, but it is not limited to these.

The solution of the ketone and the proline or proline derivative (4) is cooled to −50 deg C. to 25 deg C., and preferably to −10 to 10 deg C., and in the subsequent reaction, it is preferable to maintain this temperature.

The ketone is preferably used in an amount of 1 to 5 equiv., and particularly preferably in an amount of 2 to 3 equiv, relative to the nitroso compound.

Next, the nitroso compound expressed by formula (3) is dissolved into the above-mentioned solvent, and the solution is gradually added into the solution of the ketone and the proline or proline derivative (4).

The period of time for adding the nitroso compound solution into the solution of the ketone and the proline or proline derivative (4) is preferably 1 min to 24 hr, and particularly preferably 3 to 12 hr. For the above-mentioned super proline, the period of time is preferably 5 min to 5 hr. Also thereafter, the above-mentioned temperature is maintained while stirring 10 min to 1 hr, whereby an α-aminooxy ketone is obtained.

In this reaction, using L-proline will provide the α-aminooxy ketone with the (R) isomer being given as the major product, while using D-proline will provide the α-aminooxy ketone with the (S) isomer as the major product. Here is an example when L-proline is used.

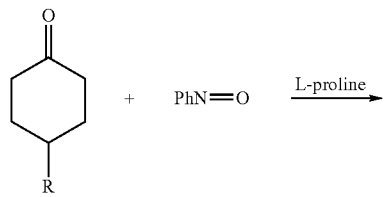

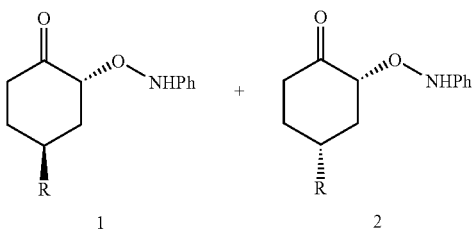

TABLE 1

| R | Yield, % | | ee, % | |
|---|---|---|---|---|
| | 1 | 2 | 1 | 2 |
| t-Bu | 32 | 32 | >99 | 94 |
| OSi-t-BuPh$_2$ | 47 | 24 | >99 | 96 |

Among the α-aminooxy ketones obtained by the method of the present invention, the following compounds and the enantiomers thereof are novel compounds, and these are useful as synthesized intermediate products which can be easily converted into α-hydroxy ketones useful for medicines, agricultural chemicals, and the like.

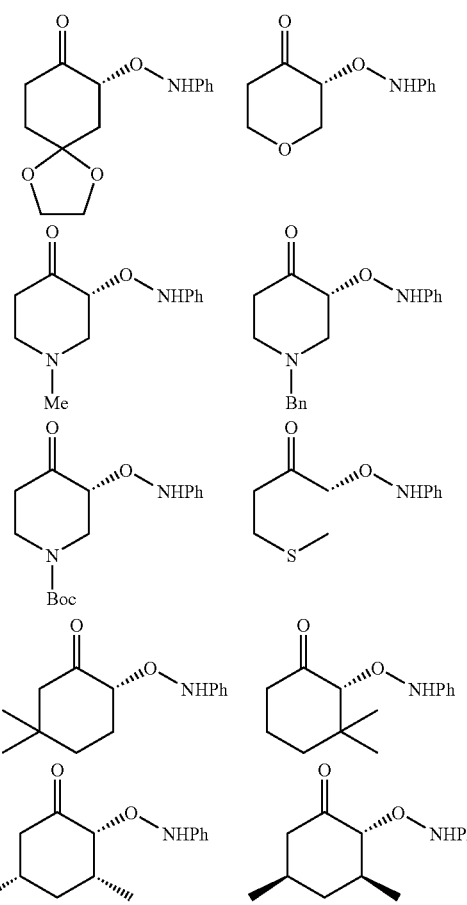

-continued

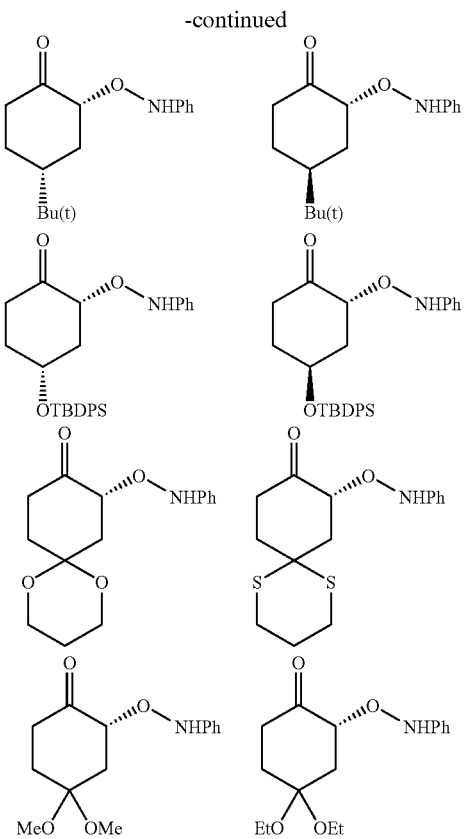

EXAMPLES

Hereinafter, the present invention will be described on the basis of EXAMPLES, however, the present invention is not limited to these EXAMPLES.

Example 1 (Table 2, No. 1)

Cyclohexanone (1.2 mmol) and L-proline (0.18 mmol) are dissolved into 2.7 mL of a DMF solution, and the solution is cooled to 0 deg C. Into this solution, a DMF solution (0.9 mL) of nitrosobenzene (0.6 mmol) is dropped over 5.5 hr. After completion of the dropping, the solution is stirred at the same temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the α-aminooxy ketone in 79% yield with ee of >99%.

The optical purity was determined by HPLC using a chiral column.

(R)-2-anilinooxy-cyclohexanone $^1$H NMR ($CDCl_3$): δ 1.37-1.75 (3H, m), 1.82-1.95 (2H, m), 4.27 (2H, dd, J=11.6, 6.2 Hz), 6.82 (3H, t, J=8.1 Hz), 7.12 (2H, t, J=7.6 Hz), 7.71 (1H, s); $^{13}$C NMR ($CDCl_3$): δ 23.6, 27.1, 32.3, 40.7, 86.1, 114.3, 114.8, 128.9, 148.0, 209.7; IR (KBr): 3041, 2942, 2865, 1716, 1600, 1494, 1132, 1099, 1072, 1027 $cm^{-1}$; HRMS(FAB): Calculated value $[C_{22}H_{15}NO_2]$: 205.1103, observed value: 205.1080; $[α]_D^{23}$ +119 (c=0.84, $CHCl_3$).

The enantiomeric excess was determined by HPLC using a Chiralpak AD-H column (hexane:2-propanol 40:1). 1.0 mL/min; major enantiomer tr=34.3 min, minor enantiomer tr=28.1 min.

Example 2 (Table 2, No. 3)

1,4-cyclohexadione monoethyleneketal (1.2 mmol) and L-proline (0.06 mmol) are dissolved into 2.7 mL of a DMF solution, and the solution is cooled to 0 deg C. Into this solution, a DMF solution (0.9 mL) of nitrosobenzene (0.6 mmol) is dropped over 12 hr. After completion of the dropping, the solution is stirred at the same temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the α-aminooxy ketone in 96% yield with ee of >99%.

The optical purity was determined by HPLC using a chiral column.

(R)-7-anilinooxy-1,4-dioxaspiro[4.5]decane-8-on $^1$H NMR ($CDCl_3$): δ 1.88-2.04 (2H, m), 2.16 (1H, t, J=12.8 Hz), 2.36-2.46 (2H, m) 2.62 (1H, dt, J=14.0, 6.8 Hz), 4.38-4.21 (4H, m), 4.60 (1H, dd, J=12.9, 6.5 Hz), 6.87 (2H, d, J=7.7 Hz), 6.90 (1H, t, J=7.2 Hz), 7.20 (2H, t, J=7.2 Hz); $^{13}$C NMR ($CDCl_3$): δ 34.9, 36.0, 39.7, 64.8, 64.9, 82.7, 107.6, 114.5, 122.2, 128.9, 148.0, 208.6; IR (neat): 2960, 2888, 1728, 1602, 1494, 1305, 1122, 1052 $cm^{-1}$; $[α]_D^{18}$ +78.7 (c=1.2, $CHCl_3$); HRMS (FAB): Calculated value $[C_{14}H_{17}NO_4]$: 263.1158, observed value: 263.1172.

The enantiomeric excess was determined by HPLC using a Chiralpak OD-H column (hexane:2-propanol 10:1). 0.5 mL/min; major enantiomer tr=26.5 min, minor enantiomer tr=29.1 min.

Example 3 (Table 2, No. 4)

4,4-dimethylcyclohexanone (1.2 mmol) and L-proline (0.06 mmol) are dissolved into 2.7 mL of a DMF solution, and the solution is cooled to 0 deg C. Into this solution, a DMF solution (0.9 mL) of nitrosobenzene (0.6 mmol) is dropped over 12 hr. After completion of the dropping, the solution is stirred at the same temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the α-aminooxy ketone in 87% yield with ee of >99%.

The optical purity was determined by HPLC using a chiral column.

(R)-2-anilinooxy-4,4-dimethylcyclohexanone $^1$H NMR ($CDCl_3$): δ 0.97 (s, 3H), 1.14 (s, 3H), 1.48-1.59 (3H, m), 4.38 (1H, ddd, J=12.7, 6.4, 3.2 Hz), 2.21-2.28 (1H, m), 2.40 (1H, dt, J=14.1, 6.5 Hz), 4.38 (1H, dd, J=12.9, 6.4 Hz), 6.79 (2H, d, J=7.8 Hz), 6, 81 (1H, t, J=8.1 Hz), 7.13 (2H, t, J=8.1 Hz); $^{13}$C NMR ($CDCl_3$): δ 24.9, 31.3, 31.9, 44.4, 83.2, 114.2, 121.9, 128.8, 148.1, 210.3; IR (KBr): 3041, 2956, 2927, 1725, 1602, 1495, 1470, 1076, 740, 692 cm$^{-1}$; $[\alpha]_D^{19}$ +85.7 (c=0.33, CHCl$_3$); HRMS (FAB): Calculated value [C$_{14}$H$_{19}$NO$_2$]: 233.1416, observed value: 233.1423.

The enantiomeric excess was determined by HPLC using a Chiralpak OD-H column (hexane:2-propanol 40:1). 1.0 mL/min; major enantiomer tr=9.1 min, minor enantiomer tr=12.2 min.

Example 4 (Table 2, No. 5)

Tetrahydro-4H-pyran-4-on (1.2 mmol) and L-proline (0.06 mmol) are dissolved into 2.7 mL of a DMF solution, and the solution is cooled to 0 deg C. Into this solution, a DMF solution (0.9 mL) of nitrosobenzene (0.6 mmol) is dropped over 12 hr. After completion of the dropping, the solution is stirred at the same temperature for 30 min. A phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 55% yield with 96% ee.

The optical purity was determined by HPLC using a chiral column.

(R)-3-anilinooxy-tetrahydropyran-4-on $^1$H NMR (CDCl$_3$): δ 2.53 (1H, dt, J=14.3, 2.9 Hz), 2.59-2.68 (1H, m), 3.60-3.72 (1H, m), 4.09-4.17 (1H, m), 4.35-4.39 (1H, m), 4.42-4.46 (1H, m), 6.86 (2H, d, J=7.7 Hz), 6.91 (1H, t, J=7.4 Hz), 7.20 (2H, t, J=7.6 Hz), 768 (1H, s); $^{13}$C NMR (CDCl$_3$): δ 42.3, 68.1, 70.1, 83.5, 114.8, 122.6, 128.9, 147.7, 205.1; IR (KBr): 2969, 2923, 2861, 2364, 1724, 1600, 1494, 1205, 1107, 694 cm$^{-1}$; $[\alpha]_D^{20}$ +47.5 (c=0.13, CHCl$_3$); HRMS (FAB): Calculated value [C$_{11}$H$_{13}$NO$_3$]: 207.0895, observed value: 207.0925.

The enantiomeric excess was determined by HPLC using a Chiralpak AD-H column (hexane:2-propanol 10:1). 1.0 mL/min; major enantiomer tr=18.6 min, minor enantiomer tr=23.7 min.

Example 5 (Table 2, No. 6)

1-methyl-4-piperidinone (1.2 mmol) and L-proline (0.06 mmol) are dissolved into 2.7 mL of a nitromethane solution, and the solution is cooled to 0 deg C. Into this solution, a nitromethane solution (0.9 mL) of nitrosobenzene (0.6 mmol) is dropped over 12 hr. After completion of the dropping, the solution is stirred at the same temperature for 30 min. A phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 45% yield with 99% ee.

The optical purity was determined by HPLC using a chiral column.

(R)-3-anilinooxy-1-methylpiperidine-4-on $^1$H NMR (CDCl$_3$): δ 2.36-2.41 (2H, m), 2.38 (3H, s), 2.54-2.64 (1H, m), 2.91-3.00 (1H, m), 3.31 (1H, dddd, J=6.4, 2.4, 2.4, 2.4 Hz), 4.49 (1H, dd, J=10.5, 6.4 Hz), 6.85-6.91 (3H, m), 7.17-7.21 (2H, m), 7.69 (1H, s); $^{13}$C NMR (CDCl$_3$): δ 40.5, 45.6, 55.8, 59.4, 83.6, 115.0, 122.8, 129.3, 148.3, 207.6 IR (neat): 2948, 2852, 2798, 1727, 1600, 1494, 1143, 1060, 904, 779, 754, 694 cm$^{-1}$; HRMS (FAB): Calculated value [C$_{12}$H$_{16}$N$_2$O$_2$]: 220.1211, observed value: 220.1248.

The enantiomeric excess was determined by HPLC using a Chiralpak AD-H column (hexane:2-propanol 10:1). 1.0 mL/min; major enantiomer tr=14.2 min, minor enantiomer tr=17.4 min.

Example 6 (Table 1, No. 1)

4-tert-butylcyclohexanone (2.2 mmol) and L-proline (0.18 mmol) are dissolved into 8.1 mL of a DMF solution, and the solution is cooled to 0 deg C. Into this solution, a DMF solution (2.7 mL) of nitrosobenzene (1.80 mmol) is dropped over 20 hr. After completion of the dropping, the solution is stirred at the same temperature for 30 min. A phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the (2R,4R)-α-aminooxy ketone and the (2R,4S)-α-aminooxy ketone as a mixture. Yield is 64%; from the analysis by NMR, the respective yields of the (2R,4R)- and (2R,4S)-isomers being 32% and 32%. By taking a part, and repeating the thin-layer chromatography a few times, the (2R,4R)- and (2R,4S)-isomers were separated from each other.

The optical purity was determined by HPLC using a chiral column.

(2R,4R)-2-anilinooxy-4-tert-butylcyclohexanone $^1$H NMR (CDCl$_3$): δ 0.83 (9H, s), 1.31 (1H, dddd, J=13.4, 4.2, 4.2, 4.2 Hz), 1.45-1.62 (2H, m), 1.93-2.02 (1H, m), 2.24 (1H, dd, J=13.7, 5.9 Hz), 2.30-2.38 (2H, m), 4.30 (1H, dd, J=12.5, 6.0 Hz), 6.78-6.85 (3H, m), 7.13 (2H, t, J=8.2 Hz), 7.76 (1H, s); $^{13}$C NMR (CDCl$_3$): δ 27.6, 32.5, 33.6, 39.7, 45.9, 85.8, 114.5, 122.0, 128.9, 148.1, 210.2; IR (neat): 2960, 2869, 1728, 1602, 1494, 1367, 1097, 742, 692 cm$^{-1}$; $[\alpha]_D^{19}$ -11.8 (c=0.87, CHCl$_3$); HRMS (FAB): Calculated value [C$_{16}$H$_{23}$NO$_2$]: 261.1729, observed value: 261.1729.

The enantiomeric excess was determined by HPLC using a Chiralpak AD-H column (hexane:2-propanol 40:1). 1.0 mL/min; major enantiomer tr=10.2 min, minor enantiomer tr=11.0 min.

(2R,4S)-2-anilinooxy-4-tert-butylcyclohexanone $^1$H NMR (CDCl$_3$): δ 0.80 (9H, s), 1.40 (1H, dddd, J=13.4, 4.2, 4.2, 4.2 Hz), 1.56-1.65 (1H, m), 1.75 (1H, tt, J=12.2, 3.5 Hz), 1.93-2.01 (1H, m), 2.16-2.18 (2H, m), 2.63 (1H, dt, J=13.9, 6.0 Hz), 4.11 (1H, t, J=4.4 Hz), 6.82 (2H, d, J=8.2 Hz), 6.85 (1H, t, J=7.3 Hz), 7.06 (1H, s), 7.15-7.18 (2H, m); $^{13}$C NMR (CDCl$_3$): δ 27.3, 32.2, 32.3, 38.0, 41.3, 84.7, 114.9, 122.6, 128.8, 147.8, 211.6; IR (neat): 2960, 2869, 1724, 1678, 1602, 1494, 1367, 1083, 748 cm$^{-1}$; $[\alpha]_D^{23}$ -53.0 (c=0.62, CHCl$_3$); HRMS (FAB): Calculated value [C$_{16}$H$_{23}$NO$_2$]: 261.1729, observed value: 261.1720.

The enantiomeric excess was determined by HPLC using a Chiralpak OD-H column(hexane:2-propanol 100:1). 1.0 mL/min; major enantiomer tr=11.1 min, minor enantiomer tr=12.5 min.

Example 7 (Table 1, No. 2)

4-tert-butyldiphenylsilyloxycyclohexanone (2.2 mmol) and L-proline (0.18 mmol) are dissolved into 8.1 mL of a DMF solution, and the solution is cooled to 0 deg C. Into this solution, a DMF solution (2.7 mL) of nitrosobenzene (1.80 mmol) is dropped over 20 hr. After completion of the dropping, the solution is stirred at the same temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the (2R,4R)-α-aminooxy ketone and the (2R,4S)-α-aminooxy ketone as a mixture. Yield is 71%; from the analysis by NMR, the respective yields of the (2R,4R)- and (2R,4S)-isomers being 47% and 24%. By taking a part, and repeating the thin-layer chromatography a few times, the (2R,4R)- and (2R,4S)-isomers were separated from each other.

The optical purity was determined by HPLC using a chiral column.

(2R,4R)-2-anilinooxy-4-(tert-butyldiphenylsiloxy)cyclohexanone $^1$H NMR ($CDCl_3$): δ 0.98 (9H, s), 1.58 (1H, t, J=12.7 Hz), 1.70 (1H, J=12.9 Hz), 1.87-1.96 (1H, m), 2.22-2.32 (2H, m), 2.84 (1H, dt, Jd=6.0, Jt=13.8 Hz), 4.23 (1H, brs), 4.81 (1H, dd, J=12.6, 6.2 Hz), 6.76 (2H, d, J=8.2 Hz), 6.83 (1H, t, J=6.9 Hz), 7.13 (2H, t, J=6.9 Hz), 7.32 (6H, m), 7.57 (4H, dd, J=15.4, 7.8 Hz), 7.69 (1H, s); $^{13}$C NMR ($CDCl_3$): δ 19.2, 27.0, 34.1, 35.7, 39.2, 67.5, 82.4, 114.5, 122.1, 127.8, 128.9, 130.0, 133.5, 135.6, 148.1, 209.9; IR (neat): 2956, 2931, 1725, 1602, 1494, 1427, 1112, 1076, 821, 701 cm$^{-1}$; $[α]_D^{18}$ +18.2 (c=0.231, $CHCl_3$); HRMS (FAB): Calculated value [$C_{28}H_{33}NO_3Si$]: 459.2230, observed value: 459.2273.

The enantiomeric excess was determined by HPLC using a Chiralpak AD-H column (hexane:2-propanol 10:1). 1.0 mL/min; major enantiomer tr=6.6 min, minor enantiomer tr=7.3 min.

(2R,4R)-2-anilinooxy-4-(tert-butyldiphenylsiloxy)cyclohexanone $^1$H NMR ($CDCl_3$): δ 1.08 (9H, s), 1.87-1.95 (1H, m), 2.00 (1H, dt, J=12.5, 10.7 Hz), 2.04-2.18 (2H, m), 2.28-2.36 (1H, m), 2.42-2.48 (1H, m), 4.09-4.18 (2H, m), 6.81 (2H, d, J=7.9 Hz), 6.93 (1H, t, J=7.9 Hz), 7.22 (2H, t, J=7.9 Hz), 7.39-7.46 (6H, m), 7.65-7.70 (4H, m), 7.53 (1H, brs); $[α]_D^{19}$ +57.8 (c=1.18, $CHCl_3$); HRMS (FAB): Calculated value [$C_{28}H_{33}NO_3Si$]: 459.2230, observed value: 459.2263.

The enantiomeric excess was determined by HPLC using a Chiralpak OD-H column (hexane:2-propanol 40:1). 1.0 mL/min; major enantiomer tr=10.3 min, minor enantiomer tr=11.3 min.

Example 8 (Table 3, Entry 1, Catalyst 10 mol %, Temperature −20 deg C.)

Into a $CH_3CN$ solution (3.0 mL) of proline (0.06 mmol), propanal (1.8 mmol) and nitrosobenzene (0.6 mmol) are added at −20 deg C., and the solution is stirred for 24 hr at the same temperature. i-PrOH (1.0 mL) and $NaBH_4$ (3 mmol) are added, and the solution is stirred for 10 min; then a phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to quantitatively obtain the β-aminoalcohol with 99% ee.

The optical purity was determined by HPLC using a chiral column.

(R)-2-anilinooxy-propanol $^1$H NMR ($CDCl_3$): δ 1.24 (3H, d, J=6.4 Hz), 2.34 (1H, brs), 3.72 (1H, dd, =12.0, 6.6 Hz), 3.80 (1H, dd, J=12.0, 2.9 Hz), 4.09-4.13 (1H, m), 6.94-6.99 (3H, m), 7.23-7.28 (2H, m); $^{13}$C NMR ($CDCl_3$): δ 15.3, 65.9, 80.0, 114.4, 122.0, 128.9, 148.5; IR (KBr): 3270, 2929, 1600, 1492, 1062, 761, 669 cm$^{-1}$; $[α]_D^{21}$ +1.8 (c=0.57, $CHCl_3$), 98% ee; HRMS (FAB): Calculated value [$C_9H_{13}NO_2$]: 167.0946, observed value: 167.0908.

The enantiomeric excess was determined by HPLC using a Chiralpak AD-H column (hexane:2-propanol 10:1). 1.0 mL/min; major enantiomer tr=10.3 min, minor enantiomer tr=9.3 min.

Example 9 (Table 3, Entry 2, Catalyst 10 mol %, Temperature −20 deg C.)

Into a $CH_3CN$ solution (3.0 mL) of proline (0.06 mmol), butanal (1.8 mmol) and nitrosobenzene (0.6 mmol) are added at −20 deg C., and the solution is stirred for 24 hr at the same temperature. i-PrOH (1.0 mL) and $NaBH_4$ (3 mmol) are added, and the solution is stirred for 10 min; then a phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the β-aminoalcohol in 88% yield with 98% ee.

The optical purity was determined by HPLC using a chiral column.

(R)-2-anilinooxy-butanol $^1$H NMR ($CDCl_3$): δ 0.98 (3H, t, J=7.5 Hz), 1.51-1.58 (1H, m), 1.65-1.70 (1H, m), 3.70-3.74 (1H, m), 3.78-3.87 (2H, m), 6.92-6.96 (3H, m), 7.23 (2H, t, J=7.6 Hz); $^{13}$C NMR ($CDCl_3$): δ 10.1, 22.9, 64.8, 85.2, 114.8, 122, 4, 128.9, 148.4; IR (KBr): 3409, 3274, 2879, 1602, 1457, 1122, 1052, 896, 767 cm$^{-1}$; $[α]_D^{16}$ +24.6 (c=0.74, $CHCl_3$), 99% ee; HRMS (FAB): Calculated value [$C_{10}H_{15}NO_2$]: 181.1103, observed value: 181.1128.

The enantiomeric excess was determined by HPLC using a Chiralpak AD-H column (hexane:2-propanol 10:1). 1.0 mL/min; major enantiomer tr=11.0 min, minor enantiomer tr=9.9 min.

Example 10 (Table 3, Entry 3, Catalyst 30 mol %, Temperature −20 deg C.)

Into a $CH_3CN$ solution (3.0 mL) of proline (0.18 mmol), pentanal (1.8 mmol) and nitrosobenzene (0.6 mmol) are added at −20 deg C., and the solution is stirred for 24 hr at the same temperature. i-PrOH (1.0 mL) and NaBH4 (3 mmol) are added, and the solution is stirred for 10 min; then a phosphate buffer solution is added to stop the reaction; organic matters are extracted with ethyl acetate; the organic phase is washed with saline, and dried with $Na_2SO_4$. After removing the Na$_2$SO$_4$ by filtration, the solvent is distilled away under reduced pressure. The product is purified by column chromatography to obtain the β-aminoalcohol in 81% yield with 98% ee.

The optical purity was determined by HPLC using a chiral column.

(R)-2-anilinooxy-pentanol $^1$H NMR (CDCl$_3$): δ 0.91 (3H, m), 1.3-1.49 (3H, m), 1.58-1.67 (1H, m), 3.69 (1H, dd, J=12.0, 6.3 Hz), 3.80 (1H, dd, J=12.0, 2.6 Hz), 3.87-3.92 (1H, m), 6.90-6.96 (3H, m), 7.19-7.23 (2H, m); $^{13}$C NMR (CDCl$_3$): δ 14.1, 18.9, 32.0, 65.0, 83.7, 114.7, 122.3, 128.9, 148.4; IR (KBr): 3400, 3282, 2958, 2933, 2873, 1602, 1494, 1465, 1124, 1027, 896, 775 cm$^{-1}$; $[α]_D^{16}$ +24.2 (c=0.34, CHCl$_3$), 98% ee; HRMS (FAB): Calculated value [C$_{11}$H$_{17}$NO$_2$]: 195.1259, observed value: 195.1247.

The enantiomeric excess was determined by HPLC using a Chiralpak AD-H column (hexane:2-propanol 10:1). 1.0 mL/min; major enantiomer tr=10.3 min, minor enantiomer tr=9.3 min.

Example 11 (Table 3, Entry 4, Catalyst 30 mol %, Temperature 0 deg C.)

Into a CH$_3$CN solution (3.0 mL) of proline (0.18 mmol), 3-methyl-butanal (1.8 mmol) and nitrosobenzene (0.6 mmol) are added at 0 deg C., and the solution is stirred for 24 hr at the same temperature. i-PrOH (1.0 mL) and NaBH$_4$ (3 mmol) are added, and the solution is stirred for 10 min; then a phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the β-aminoalcohol in 77% yield with 97% ee.

The optical purity was determined by HPLC using a chiral column.

(R)-3-methyl-2-anilinooxy-butanol $^1$H NMR (CDCl$_3$): δ 0.99 (3H, d, J=6.9 Hz), 1.03 (3H, d, J=6.9 Hz), 1.99-2.04 (1H, m), 3.70-3.74 (1H, m), 3.81-3.86 (2H, m), 6.95-7.01 (3H, m), 7.23-7.28 (2H, m); $^{13}$C NMR (CDCl$_3$): δ 19.0, 19.2, 29.2, 64.2, 89.0, 115.5, 123.0, 129.4, 148.7; IR (KBr): 3397, 3272, 2962, 2933, 2875, 1602, 1494, 1469, 1051, 1025, 898, 742, 692 cm$^{-1}$; $[α]_D^{16}$ +35.8 (c=0.42, CHCl$_3$), 99% ee; HRMS (FAB): Calculated value [C$_{11}$H$_{17}$NO$_2$]: 195.1259, observed value: 195.1280.

The enantiomeric excess was determined by HPLC using a Chiralpak AD-H column (hexane:2-propanol 10:1). 1.0 mL/min; major enantiomer tr=9.4 min, minor enantiomer tr=8.4 min.

Example 12 (Table 3, Entry 5, Catalyst 30 mol %, Temperature 0 deg C.)

Into a CH$_3$CN solution (3.0 mL) of proline (0.18 mmol), 3-phenyl-propanal (1.8 mmol) and nitrosobenzene (0.6 mmol) are added at 0 deg C., and the solution is stirred for 24 hr at the same temperature. i-PrOH (1.0 mL) and NaBH$_4$ (3 mmol) are added, and the solution is stirred for 10 min; then a phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the β-aminoalcohol in 72% yield with 99% ee.

The optical purity was determined by HPLC using a chiral column.

(R)-3-phenyl-2-anilinooxy-propanol $^1$H NMR (CDCl$_3$): δ 2.25 (1H, brs), 2.77 (1H, dd, J=13.7, 6.9 Hz), 2.95 (1H, dd, J=13.7, 6.9 Hz), 3.65 (1H, dd, J=11.8, 5.8 Hz), 3.77 (1H, d, J=11.8 Hz), 4.06 (1H, m), 6.76 (1H, d, J=8.0 Hz), 6.86 (1H, t, J=8.0 Hz), 6.94 (1H, brs), 7.10-7.23 (7H, m); $^{13}$C NMR (CDCl$_3$): δ 36.5, 64.2, 85.0, 114.8, 122.5, 126.5, 128.5, 128.9, 129.4, 137.8, 148.3; IR (KBr): 3390, 3280, 1600, 1494, 1454, 1240, 1083, 1070, 1029, 898, 767, 744, 694 cm$^{-1}$; $[α]_D^{16}$ +63.3 (c=0.71, CHCl$_3$), 99% ee; HRMS (FAB): Calculated value [C$_{15}$H$_{17}$NO$_2$]: 243.1259, observed value: 243.1228.

The enantiomeric excess was determined by HPLC using a Chiralpak AD-H column (hexane:2-propanol 10:1). 1.0 mL/min; major enantiomer tr=16.4 min, minor enantiomer tr=13.6 min.

Example 13 (Table 3, Entry 6, Catalyst 30 mol %, Temperature −20 deg C.)

Into a CH$_3$CN solution (3.0 mL) of proline (0.18 mmol), phenyl acetaldehyde (1.8 mmol) and nitrosobenzene (0.6 mmol) are added at −20 deg C., and the solution is stirred for 24 hr at the same temperature. i-PrOH (1.0 mL) and NaBH$_4$ (3 mmol) are added, and the solution is stirred for 10 min; then a phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain β-aminoalcohol in 62% yield with 99% ee.

The optical purity was determined by HPLC using a chiral column.

(R)-2-phenyl-2-anilinooxy-ethanol $^1$H NMR (CDCl$_3$): δ 2.52 (1H, brs), 3.77 (1H, dd, J=12.2, 3.3 Hz), 3.93 (1H, dd, J=12.2, 8.1 Hz), 4.97 (1H, dd, J=8.1, 3.3 Hz), 6.92-6.95 (4H, m), 7.20-7.24 (2H, m), 7.31-7.38 (5H, m); $^{13}$C NMR (CDCl$_3$): δ 63.3, 86.5, 115.0, 122.5, 127.1, 128.4, 128.7, 129.0, 137.8, 147.9; IR (KBr): 3272, 3031, 2921, 1600, 1494, 1454, 1309, 1072, 1027, 896, 759 cm$^{-1}$; $[α]_D^{17}$ −126.5 (c=0.52, CHCl$_3$), 99% ee; HRMS (FAB): Calculated value [C$_{14}$H$_{15}$NO$_2$]: 229.1103, observed value: 229.1111.

The enantiomeric excess was determined by HPLC using a Chiralpak OD-H column (hexane:2-propanol 10:1). 1.0 mL/min; major enantiomer tr=10.5 min, minor enantiomer tr=11.6 min.

Examples in Table 4

Example 14 (Table 4, Entry 1)

Into a DMF solution (2.7 mL) of 3,3-dimethylcyclohexanone (1.2 mmol) and proline (0.06 mmol), a DMF solution (0.9 mL) of nitrosobenzene (0.6 mmol) is added at 0 deg C. over 38 hr, and the solution is stirred for 0.5 hr at the same temperature. A phosphate buffer solution is added to stop the reaction; organic matters are extracted three times with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 43% yield with 99% ee. Diastereomer ratio is 88:12.

The optical purity was determined by HPLC using a chiral column.

(R)-2-anilinooxy-5,5-dimethylcyclohexanone $^1$H NMR (CDCl$_3$): δ 0.92 (3H, s), 1.06 (3H, s), 1.63-167 (1H, m), 1.63-1.96 (2H, m), 1.96 (1H, dq, J=12.7, 4.8 Hz), 2.21 (1H, dt, J=13.1, 2.5 Hz), 2.25-2.31 (2H, m), 4.33 (1H, dd, J=12.1, 7.1 Hz), 6.89-6.94 (3H, m), 7.21-7.25 (2H, m), 7.77 (1H, brs); $^{13}$C NMR (CDCl$_3$): δ 25.4, 27.8, 31.2, 36.6, 36.8, 53.5, 85.6, 114.5, 122.1, 128.9, 148.1, 209.5; IR (KBr): 2960, 2923, 1718, 1602, 1496, 1103, 1079, 794, 757, 692 cm$^{-1}$; HRMS (FAB): Calculated value [C$_{14}$H$_{19}$NO$_2$]: 233.1473, observed value: 233.1395; [α]$_D^{24}$ +132.1 (c=0.43, CHCl$_3$).

The enantiomeric excess was determined by HPLC using a Chiralpak AD-H column (hexane:2-propanol 10:1). 1.0 mL/min; major enantiomer tr=17.7 min, minor enantiomer tr=14.6 min.

Example 15 (Table 4, Entry 2)

Into a DMF solution (2.7 mL) of cys-3,5-dimethylcyclohexanone (1.2 mmol) and proline (0.06 mmol), a DMF solution (0.9 mL) of nitrosobenzene (0.6 mmol) is added at 0 deg C. over 26 hr, and the solution is stirred for 0.5 hr at the same temperature. A phosphate buffer solution is added to stop the reaction; organic matters are extracted three times with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 60% yield with 99% ee. Diastereomer ratio is 70:30.

The optical purity was determined by HPLC using a chiral column.

(2R,3R,5S)-2-anilinooxy-3,5-dimethylcyclohexanone $^1$H NMR (CDCl$_3$): δ 1.04 (3H, d, J=6.5 Hz), 1.21 (3H, d, J=7.0 Hz), 1.53-1.59 (2H, m), 1.77-1.96 (2H, m), 2.22 (1H, dd, J=12.5, 3.9 Hz), 2.52 (1H, t, J=12.5 Hz), 3.98 (1H, d, J=1.2 Hz), 6.90-6.98 (3H, m), 7.22-7.26 (2H, m); $^{13}$C NMR (CDCl$_3$): δ 17.6, 19.1, 22.3, 34.3, 37.6, 38.5, 45.5, 89.8, 114.9, 122.6, 128.9, 147.9, 211.4; IR (KBr): 3268, 2960, 2927, 1716, 1494, 1455, 1284, 769, 738, 692 cm$^{-1}$; HRMS (FAB): Calculated value [C$_{14}$H$_{19}$NO$_2$]: 233.1416, observed value: 233.1431; [α]$_D^{24}$ +48.1 (c=0.57, CHCl$_3$).

The enantiomeric excess was determined by HPLC using a Chiralpak AD-H column (hexane:2-propanol 10:1). 1.0 mL/min; major enantiomer tr=10.7 min, minor enantiomer tr=9.8 min.

The absolute configuration was determined by converting a diol obtained by causing NaBH$_4$ to act on 13a into (1S,2R,3R,5S)-1,2-bis(p-bromobenzoyloxy)-3,5-dimethylcyclohexane, and applying the CD-chirality method thereto.

(2R,3S,5R)-2-anilinooxy-3,5-dimethylcyclohexanone $^1$H NMR (CDCl$_3$): δ 1.02 (3H, d, J=6.2 Hz), 1.29 (3H, d, J=6.3 Hz), 1.86-2.02 (4H, m), 2.09 (1H, t, J=13.0 Hz), 2.38-2.42 (1H, m), 4.05 (1H, d, J=11.4 Hz), 6.90-6.94 (3H, m), 7.21-7.25 (2H, m), 7.95 (1H, brs); $^{13}$C NMR (CDCl$_3$): δ 19.5, 22.0, 33.5, 37.8, 41.8, 48.6, 91.2, 114.6, 122.0, 128.9, 148.2, 209.4; IR (KBr): 3307, 2954, 1720, 1602, 1496, 1097, 887, 761, 738, 694, 582, 501 cm$^{-1}$; HRMS (FAB): Calculated value [C$_{14}$H$_{19}$NO$_2$]: 233.2416, observed value: 233.1400; [α]$_D^{24}$ +183.6 (c=0.36, CHCl$_3$).

The enantiomeric excess was determined by HPLC using a Chiralpak AD-H column (hexane:2-propanol 10:1). 1.0 mL/min; major enantiomer tr=31.1 min, minor enantiomer tr=15.3 min.

The absolute configuration was determined by converting a diol obtained by causing NaBH$_4$ to act on 13b into (1S,2R,3S,5R)-1,2-bis(p-bromobenzoyloxy)-3,5-dimethylcyclohexane, and applying the CD-chirality method thereto.

Example 16 (Table 4, Entry 4)

Into a DMF solution (2.7 mL) of 3-phenylcyclohexanone (1.2 mmol) and proline (0.06 mmol), a DMF solution (0.9 mL) of nitrosobenzene (0.6 mmol) is added at 0 deg C. over 29 hr, and the solution is stirred for 0.5 hr at the same temperature. A phosphate buffer solution is added to stop the reaction; organic matters are three times extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 72% yield with 99% ee for the major product. Diastereomer ratio is 32:32:32:4.

The optical purity was determined by HPLC using a chiral column.

(2R,5R)-2-anilinooxy-5-phenylcyclohexanone $^1$H NMR (CDCl$_3$): δ 1.85-2.03 (2H, m), 2.14-2.18 (1H, m), 2.50-2.57 (1H, m), 2.60-2.69 (2H, m), 2.96-3.04 (1H, m), 4.52 (1H, dd, J=11.9, 6.2 Hz); $^{13}$C NMR (CDCl$_3$): δ 31.2, 31.7, 45.3, 48.0, 85.9, 114.5, 122.2, 126.4, 127.0, 128.8, 128.9, 143.3, 148.1, 208.4; IR(KBr): 3278, 2952, 1718, 1604, 1494, 1415, 1029, 794, 748, 694 cm$^{-1}$; HRMS (FAB): Calculated value [C$_{18}$H$_{19}$NO$_2$]: 281.1416, observed value: 281.1396; [α]$_D^{23}$ +91.6 (c=0.41, CHCl$_3$).

The enantiomeric excess was determined by HPLC using a Chiralpak AD-I column (hexane:2-propanol 10:1). 1.0 mL/min; major enantiomer tr=22.4 min, minor enantiomer tr=18.4 min.

Example 17 (Table 5, Entry 5)

Into a DMF solution (2.7 mL) of 3-(4-tert-butylphenylthio)cyclohexanone (1.2 mmol) and proline (0.06 mmol), a DMF solution (0.9 mL) of nitrosobenzene (0.6 mmol) is added at 0 deg C. over 13 hr, and the solution is stirred for 0.5 hr at the same temperature. A phosphate buffer solution is added to stop the reaction; organic matters are extracted three times with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 61% yield with 99% ee for the major product. Diastereomer ratio is 46:21:33.

The optical purity was determined by HPLC using a chiral column.

(2R,5S)-2-anilinooxy-5-(4-tert-butylphenylthio)cyclohexanone $^1$H NMR (CDCl$_3$): δ 1.28 (9H, s), 1.55-1.65 (1H, m), 1.72-1.86 (1H, m), 1.94-2.05 (1H, m), 2.18-2.37 (2H, m), 2.43-2.52 (1H, m), 3.35 (1H, dddd, J=11.5, 11.5, 4.3, 4.3 Hz), 4.26 (1H, d, J=11.2 Hz), 6.94 (1H, t, J=7.1 Hz), 7.17 (2H, d, J=7.7 Hz), 7.21-7.28 (2H, m), 7.30 (2H, d, J=8.4 Hz), 7.44 (2H, d, J=8.4 Hz); $^{13}$C NMR (CDCl$_3$): δ 24.6, 31.2, 32.1, 34.6, 40.3, 51.0, 88.6, 114.9, 122.2, 126.1, 126.3, 128.9, 134.2, 135.1, 148.1, 151.5, 207.4; IR (KBr): 2960, 1727, 1600, 1494, 1120, 1014, 904, 829, 740, 694 cm$^{-1}$; HRMS (FAB): Calculated value [C$_{22}$H$_{27}$NO$_2$S]: 369.1763, observed value: 369.1769; [α]$_D^{23}$ +56.5 (c=0.27, CHCl$_3$).

The enantiomeric excess was determined by HPLC using a Chiralpak OD-H column (hexane:2-propanol 10:1). 1.0 mL/min; major enantiomer tr=15.0 min, minor enantiomer tr=13.9 min.

(2R,5R)-2-anilinooxy-5-(4-tert-butylphenylthio)cyclohexanone $^1$H NMR (CDCl$_3$): δ 1.30 (9H, s), 1.73-1.90 (2H, m), 2.23-2.35 (1H, m), 2.35-2.50 (2H, m), 2.71-2.82 (2H, m), 3.15-3.28 (1H, m), 4.37 (1H, dd, J=11.3, 6.2 Hz), 6.85-6.96 (3H, m), 7.18-7.27 (2H, m), 7.30-7.38 (4H, m), 7.74 (1H, brs); $^{13}$C NMR (CDCl$_3$): δ 30.1, 30.7, 31.2, 34.6, 46.3, 47.3, 85.6, 114.5, 122.3, 126.2, 128.7, 128.9, 133.8, 147.9, 151.6, 206.7; IR (KBr): 2960, 1724, 1601, 1495, 1400, 1269, 1120, 930, 829, 692 cm$^{-1}$; HRMS (FAB): Calculated value [C$_{22}$H$_{27}$NO$_2$S]: 369.1763, observed value: 369.1760; [α]$_D^{23}$ +118.1 (c=0.28, CHCl$_3$).

The enantiomeric excess was determined by HPLC using a Chiralpak OD-H column (hexane:2-propanol 10:1). 1.0 mL/min; major enantiomer tr=22.5 min, minor enantiomer tr=19.1 min.

(2S,3S)-2-anilinooxy-3-(4-tert-butylphenylthio)cyclohexanone $^1$H NMR (CDCl$_3$): δ 1.25 (9H, s), 2.02-2.20 (3H, m), 2.28-2.45 (1H, m), 2.63 (2H, d, J=4.9 Hz), 3.61-3.75 (1H, m), 4.27 (1H, dd, J=4.6, 10.3 Hz), 6.80-6.97 (3H, m), 7.15-7.26 (2H, m), 7.25-7.40 (4H, m), 7.56-7.72 (1H, brs); $^{13}$C NMR (CDCl$_3$): δ 27.8, 28.9, 31.2, 34.6, 44.9, 46.7, 85.4, 114.7, 122.3, 126.2, 128.9, 129.6, 133.3, 147.9, 151.3, 207.0; IR (KBr): 2960, 1722, 1600, 1494, 1396, 1269, 1110, 829, 757, 692 cm$^{-1}$; HRMS (FAB): Calculated value [C$_{22}$H$_{27}$NO$_2$S]: 369.1763, observed value: 369.1761; [α]$_D^{23}$ +16.5 (c=0.24, CHCl$_3$).

The enantiomeric excess was determined by HPLC using a Chiralpak AD-H column (hexane:2-propanol 10:1). 1.0 mL/min; major enantiomer tr=17.1 min, minor enantiomer tr=13.8 min.

Example 18 (Table 5, Entry 6)

Into a DMF solution (8.1 mL) of 4-tert-butylcyclohexanone (2.2 mmol) and proline (0.18 mmol), a DMF solution (2.7 mL) of nitrosobenzene (1.8 mmol) is added at 0 deg C. over 32 hr, and the solution is stirred for 0.5 hr at the same temperature. A phosphate buffer solution is added to stop the reaction; organic matters are extracted three times with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 62% yield with 99% ee for the major product. Diastereomer ratio is 50:50.

The optical purity was determined by HPLC using a chiral column.

(2R,4R)-2-anilinooxy-4-tert-butylcyclohexanone $^1$H NMR (CDCl$_3$): δ 0.83 (9H, s), 1.31 (1H, dddd, J=13.4, 4.2, 4.2, 4.2 Hz), 1.45-1.62 (2H, m), 1.93-2.02 (1H, m), 2.24 (1H, dd, J=13.7, 5.9 Hz), 2.30-2.38 (2H, m), 4.30 (1H, dd, J=12.5, 6.0 Hz), 6.78-6.85 (3H, m), 7.13 (2H, t, J=8.2 Hz), 7.76 (1H, s); $^{13}$C NMR (CDCl$_3$): δ 27.6, 32.5, 33.6, 39.7, 45.9, 85.8, 114.5, 122.0, 128.9, 148.1, 210.2; IR (neat): 2960, 2869, 1728, 1602, 1494, 1367, 1097, 742, 692 cm$^{-1}$; [α]$_D^{20}$ +79.4 (c=0.33, CHCl$_3$), >99% ee; HRMS (FAB): Calculated value [C$_{16}$H$_{23}$NO$_2$]: 261.1729, observed value: 261.1729.

The enantiomeric excess was determined by HPLC using a Chiralpak AD-H column (hexane:2-propanol 40:1). 1.0 mL/min; major enantiomer tr=10.2 min, minor enantiomer tr=11.0 min.

(2R,4S)-2-anilinooxy-4-tert-butylcyclohexanone $^1$H NMR (CDCl$_3$): δ 0.80 (9H, s), 1.40 (1H, dddd, J=13.4, 4.2, 4.2, 4.2 Hz), 1.56-1.65 (1H, m), 1.75 (1H, tt, J=12.2, 3.5 Hz), 1.93-2.01 (1H, m), 2.16-2.18 (2H, m), 2.63 (1H, dt, J=13.9, 6.0 Hz), 4.11 (1H, t, J=4.4 Hz), 6.82 (2H, d, J=8.2 Hz), 6.85 (1H, t, J=7.3 Hz), 7.06 (1H, s), 7.15-7.18 (2H, m); $^{13}$C NMR (CDCl$_3$): δ 27.3, 32.2, 32.3, 38.0, 41.3, 84.7, 114.9, 122.6, 128.8, 147.8, 211.6; IR (neat): 2960, 2869, 1724, 1673, 1602, 1494, 1367, 1083, 748 cm$^{-1}$; [α]$_D^{19}$ −11.8 (c=0.87, CHCl$_3$), 94% ee; HRMS (FAB): Calculated value [C$_{16}$H$_{23}$NO$_2$]: 261.1729, observed value: 261.1720.

The enantiomeric excess was determined by HPLC using a Chiralpak OD-H column (hexane:2-propanol 100:1). 1.0 mL/min; major enantiomer tr=11.1 min, minor enantiomer tr=12.5 min.

Example 19 (Table 5, Entry 7)

Into a DMF solution (8.1 mL) of 4-(tert-butyldiphenylsiloxy)cyclohexanone (2.2 mmol) and proline (0.18 mmol), a DMF solution (2.7 mL) of nitrosobenzene (1.8 mmol) is added at 0 deg C. over 32 hr, and the solution is stirred for 0.5 hr at the same temperature. A phosphate buffer solution is added to stop the reaction; organic matters are extracted three times with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 69% yield with 99% ee for the major product. Diastereomer ratio is 67:33.

The optical purity was determined by HPLC using a chiral column.

(2R,4R)-2-anilinooxy-4-(tert-butyldiphenylsiloxy)cyclohexanone $^1$H NMR (CDCl$_3$): δ 0.98 (9H, s), 1.58 (1H, t, J=12.7 Hz), 1.70 (1H, J=12.9 Hz), 1.87-1.96 (1H, m), 2.22-2.32 (2H, m), 2.84 (1H, dt, Jd=6.0, Jt=13.8 Hz), 4.23 (1H, brs), 4.81 (1H, dd, J=12.6, 6.2 Hz), 6.76 (2H, d, J=8.2 Hz), 6.83 (1H, t, J=6.9 Hz), 7.13 (2H, t, J=6.9 Hz), 7.32 (6H, m), 7.57 (4H, dd, J=15.4, 7.8 Hz), 7.69 (1H, s); $^{13}$C NMR (CDCl$_3$): δ 19.2, 27.0, 34.1, 35.7, 39.2, 67.5, 82.4, 114.5, 122.1, 127.8, 128.9, 130.0, 133.5, 135.6, 148.1, 209.9; IR (neat): 2956, 2931, 1725, 1602, 1494, 1427, 1112, 1076, 821, 701 cm$^{-1}$; $[\alpha]_D^{18}$ +18.2 (c=0.23, CHCl$_3$), >99% ee; HRMS (FAB): Calculated value [C$_{28}$H$_{33}$NO$_3$Si]: 459.2230, observed value: 459.2273.

The enantiomeric excess was determined by HPLC using a Chiralpak AD-H column (hexane:2-propanol 40:1). 1.0 mL/min; major enantiomer tr=6.6 min, minor enantiomer tr=7.3 min.

(2R,4S)-2-anilinooxy-4-(tert-butyldiphenylsiloxy)cyclohexanone $^1$H NMR (CDCl$_3$): δ 1.08 (9H, s), 1.87-1.95 (1H, m), 2.00 (1H, dt, J=12.5, 10.7 Hz), 2.04-2.18 (2H, m), 2.28-2.36 (1H, m), 2.42-2.48 (1H, m), 4.09-4.18 (2H, m), 6.81 (2H, d, J=7.9 Hz), 6.93 (1H, t, J=7.9 Hz), 7.22 (2H, t, J=7.9 Hz), 7.39-7.46 (6H, m), 7.65-7.70 (4H, m), 7.53 (1H, brs); $[\alpha]_D^{19}$ +57.8 (c=1.18, CHCl$_3$), 96% ee; HRMS (FAB): Calculated value [C$_{28}$H$_{33}$NO$_3$Si]: 459.2230, observed value: 459.2263.

The enantiomeric excess was determined by HPLC using a Chiralpak OD-H column (hexane:2-propanol 40:1). 1.0 mL/min; major enantiomer tr=10.3 min, minor enantiomer tr=11.3 min.

The results in the above EXAMPLES are given in the above Table 1 to the following Table 5.

TABLE 2

| No. | Ketone | Product | Yield, % | ee, % |
|---|---|---|---|---|
| 1 | cyclohexanone | 2-(anilinooxy)cyclohexanone | 79 | >99[a] |
| 2 | cyclohexanone | 2-(anilinooxy)cyclohexanone | 77 | >99 |
| 3 | 1,4-dioxaspiro[4.5]decan-8-one | α-aminooxy derivative | 96 | >99 |
| 4 | 4,4-dimethylcyclohexanone | α-aminooxy derivative | 87 | >99 |
| 5 | tetrahydro-4H-pyran-4-one | α-aminooxy derivative | 55 | 96 |
| 6 | 1-methylpiperidin-4-one | α-aminooxy derivative | 45 | 99 |
| 7 | 1-benzylpiperidin-4-one | α-aminooxy derivative | 45 | >99 |
| 8 | 1-Boc-piperidin-4-one | α-aminooxy derivative | 41 | >99 |
| 9 | tetrahydro-4H-thiopyran-4-one | α-aminooxy derivative | 69 | >99 |

[a] catalyst 30 mol %; for the others, catalyst 10 mol %
[c] Amount of catalyst 10 mol %

As can be seen from the above table, when cyclohexanone or dimethylcyclohexanone is used as a ketone, the corresponding α-aminooxy ketone derivative was obtained in a high yield with a high enantioselectivity. In addition, even with a ketone having the acetal site at the 4-position, the corresponding α-aminooxy ketone derivative was obtained in a high yield with a high enantioselectivity.

TABLE 3
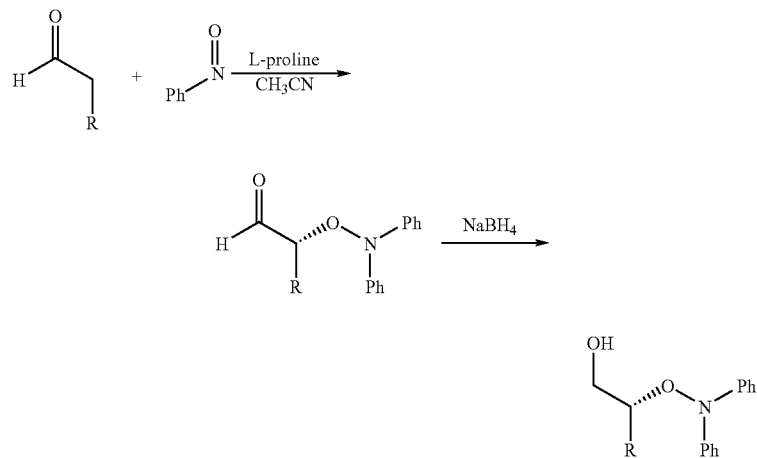
| Entry | R | 10 mol % Yld, % | 0 deg C. ee, % | 30 mol % Yld, % | 0 deg C. ee, % | 10 mol % Yld, % | −20 deg C. ee, % | 30 mol % Yld, % | −20 deg C. ee, % |
|---|---|---|---|---|---|---|---|---|---|
| 1 | Me | 81 | 98 | 80 | 98 | quant | 98 | quant | 98 |
| 2 | Et | 64 | 98 | 64 | 98 | 88 | 98 | 87 | 99 |
| 3 | n-Pr | 55 | 98 | 71 | 97 | 53 | 97 | 81 | 98 |
| 4 | i-Pr | 72 | 98 | 77 | 97 | 77 | 99 | 77 | 99 |
| 5 | CH$_2$Ph | 67 | 98 | 72 | 99 | <5 | | 70 | 99 |
| 6 | Ph | 20 | | 44 | 99 | <5 | | 62 | 99 |
TABLE 4
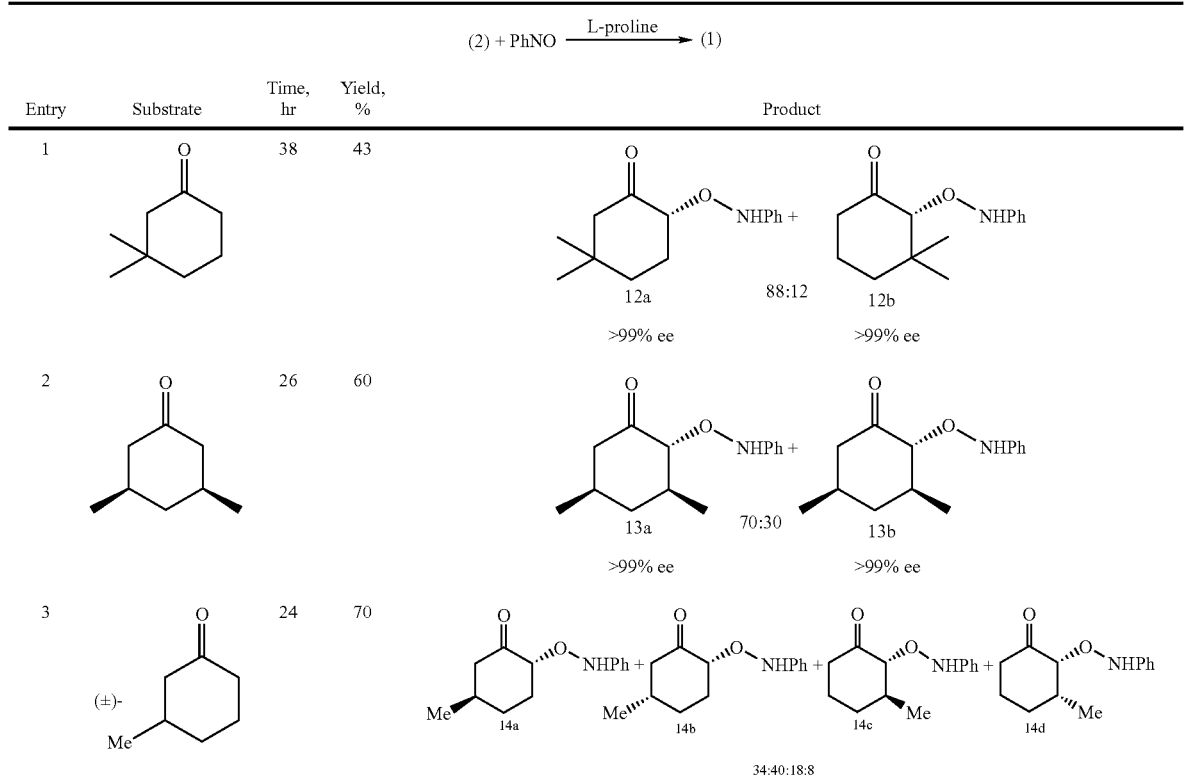

TABLE 4-continued (2) + PhNO —L-proline→ (1)

| Entry | Substrate | Time, hr | Yield, % | Product |
|---|---|---|---|---|
| 4 | (±)-3-phenylcyclohexanone | 29 | 72 | 15a + 15b + 15c + 15d  32:32:32:4 |

TABLE 5

(2) + PhNO —L-proline→ (1)

| Entry | Substrate | Time, hr | Yield, % | Product |
|---|---|---|---|---|
| 5 | (±)-3-(4-tert-butylphenylthio)cyclohexanone | 13 | 61 | 16a (>99% ee) + 16b (>99% ee) + 16c (>97% ee)  46:21:33  R = p-tert-butylphenyl |
| 6 | 4-tert-butylcyclohexanone | 32 | 62 | 17a (>99% ee) + 17b (94% ee)  50:50 |
| 7 | 4-OTBDPS-cyclohexanone | 32 | 69 | 18a (>99% ee) + 18b (94% ee)  67:33 |

Experiments for Table 6

Example 20 (Table 6, Entry 1)

Cyclohexanone (1.2 mmol) and 4-tert-butyldimethylsiloxy-L-proline (super proline) (0.06 mmol) are dissolved into 1.0 mL of a DMF solution, and into this solution, a DMF solution (0.5 mL) of nitrosobenzene (0.6 mmol) is dropped over 15 min. After completion of the dropping, the solution is stirred at room temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the α-aminooxy ketone in 76% yield with ee of >99%.

The optical purity was determined by HPLC using a chiral column.

(R)-2-anilinooxy-cyclohexanone $^1$H NMR (CDCl$_3$): δ 1.37-1.75 (3H, m), 1.82-1.95 (2H, m), 4.27 (2H, dd, J=11.6, 6.2 Hz), 6.82 (3H, t, J=8.1 Hz), 7.12 (2H, t, J=7.6 Hz), 7.71 (1H, s); $^{13}$C NMR (CDCl$_3$): δ 23.6, 27.1, 32.3, 40.7, 86.1, 114.3, 114.8, 128.9, 148.0, 209.7; IR (KBr): 3041, 2942, 2865, 1716, 1600, 1494, 1132, 1099, 1072, 1027 cm$^{-1}$; HRMS (FAB): Calculated value [C$_{12}$H$_{15}$NO$_2$]: 205.1103, observed value: 205.1080; [α]$_D^{23}$ +119 (c=0.84, CHCl$_3$).

HPLC: Chiralpak AD-H column (hexane:2-propanol 40:1). 1.0 mL/min; major enantiomer tr=34.3 min, minor enantiomer tr=28.1 min.

Example 21 (Table 6, Entry 2)

4,4-dimethylcyclohexanone (1.2 mmol) and super proline (0.06 mmol) are dissolved into 1.0 mL of a DMF solution, and into this solution, a DMF solution (0.5 mL) of nitrosobenzene (0.6 mmol) is dropped over 2 hr. After completion of the dropping, the solution is stirred at room temperature for 30 min. A phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 74% yield with ee of >99%.

The optical purity was determined by HPLC using a chiral column.

(R)-2-anilinooxy-4,4-dimethylcyclohexanone $^1$H NMR (CDCl$_3$): δ 0.97 (s, 3H), 1.14 (s, 3H), 1.48-1.59 (3H, m), 4.38 (1H, ddd, J=12.7, 6.4, 3.2 Hz), 2.21-2.28 (1H, m), 2.40 (1H, dt, J=14.1, 6.5 Hz), 4.38 (1H, dd, J=12.9, 6.4 Hz), 6.79 (2H, d, J=7.8 Hz), 6.81 (1H, t, J=8.1 Hz), 7.13 (2H, t, J=8.1 Hz); $^{13}$C NMR (CDCl$_3$): δ 24.9, 31.3, 31.9, 44.4, 83.2, 114.2, 121.9, 128.8, 148.1, 210.3; IR (KBr): 3041, 2956, 2927, 1725, 1602, 1495, 1470, 1076, 740, 692 cm$^{-1}$; [α]$_D^{19}$ +85.7 (c=0.33, CHCl$_3$); HRMS (FAB): Calculated value [C$_{14}$H$_{19}$NO$_2$]: 233.1416, observed value: 233.1423.

HPLC: Chiralcel OD-H column (hexane:2-propanol 40:1). 1.0 mL/min; major enantiomer tr=9.1 min, minor enantiomer tr=12.2 min.

Example 22 (Table 6, Entry 3)

Tetrahydrothiopyran-4-on (1.2 mmol) and super proline (0.06 mmol) are dissolved into 1.0 mL of a DMF solution, and into this solution, a DMF solution (0.5 mL) of nitrosobenzene (0.6 mmol) is dropped over 2 hr. After completion of the dropping, the solution is stirred at room temperature for 30 min. A phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 68% yield with ee of >99%.

The optical purity was determined by HPLC using a chiral column. (R)-3-anilinooxy-tetrahydrothiopyran-4-on $^1$H NMR (CDCl$_3$): δ 2.76-2.95 (4H, m), 3.04 (1H, dd, J=11.5, 13.0 Hz), 3.19 (1H, dd, J=5.4, 13.0 Hz), 4.63 (1H, dd, J=5.4, 11.5 Hz), 6.90-6.97 (3H, m), 7.22-7.26 (2H, m), 7.68 (1H, brs); $^{13}$C NMR (CDCl$_3$): δ 30.2, 33.8, 44.9, 86.4, 114.6, 122.4, 128.9, 147.8, 206.3; IR (KBr): 3262, 2925, 1724, 1602, 1494, 1469, 1415, 1309, 1101, 1076, 993, 783, 692 cm$^{-1}$; HRMS (FAB): Calculated value [C$_{11}$H$_{13}$NO$_2$S]: 223.0667, observed value: 223.0667; [α]$_D^{21}$ +85.7 (c=0.69, CHCl$_3$).

The enantiomeric excess was determined by HPLC using a Chiralpak AS-H column (hexane:2-propanol 10:1). 1.0 mL/min; major enantiomer tr=19.9 min, minor enantiomer tr=22.6 min.

Example 23 (Table 6, Entry 4)

Cycloheptanone (1.2 mmol) and super proline (0.06 mmol) are dissolved into 1.0 mL of a DMF solution, and into this solution, a DMF solution (1.0 mL) of nitrosobenzene (0.6 mmol) is dropped over 2 hr. After completion of the dropping, the solution is stirred at room temperature for 30 min. A phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 45% yield with ee of >99%.

The optical purity was determined by HPLC using a chiral column.

(R)-2-anilinooxy-cycloheptanone $^1$H NMR (CDCl$_3$): δ 1.32-1.44 (1H, m), 1.59-1.78 (3H, m), 1.79-1.91 (3H, m), 2.05-2.12 (1H, m), 2.41-2.51 (1H, m), 2.52-2.61 (1H, m), 4.60 (1H, dd, J=9.4, 3.9 Hz), 6.87-6.97 (3H, m), 7.20-7.32 (2H, m), 7.53 (1H, bs); $^{13}$C NMR (CDCl$_3$): δ 23.1, 26.5, 28.6, 30.0, 41.1, 88.2, 114.4, 122.1, 128.9, 148.0, 211.6; IR (KBr): 3021, 2979, 2402, 1752, 1603, 1520, 1472, 1215, 1026, 930 cm$^{-1}$; [α]$_D^{22}$ +59.9 (c=0.61, CHCl$_3$); HRMS (FAB): Calculated value [C$_{13}$H$_{17}$NO$_2$]: 219.1259, observed value: 219.1235.

The enantiomeric excess was determined by HPLC using a (Chiralcel) AD-H column (hexane:2-propanol 10:1). 1.0 mL/min; major enantiomer tr=20.2 min, minor enantiomer tr=16.2 min.

Example 24 (Table 6, Entry 5)

3-pentanone (6 mmol) and super proline (0.06 mmol) are dissolved into 1.0 mL of a DMF solution, and into this solution, a DMF solution (1.0 mL) of nitrosobenzene (0.6 mmol) is dropped over 1 hr. After completion of the dropping, the solution is stirred at room temperature for 30 min. A phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminooxy ketone in 50% yield with ee of >99%.

The optical purity was determined by HPLC using a chiral column.

(R)-2-anilinooxy-3-pentanone $^1$H NMR (CDCl$_3$): δ 1.09 (3H, t, J=7.3 Hz), 1.41 (3H, d, J=7.0 Hz), 2.53 (2H, q, J=7.3 Hz), 4.45 (1H, q, J=7.0 Hz), 6.89-6.99 (3H, m), 7.21-7.28 (2H, m), 7.30 (1H, bs); $^{13}$C NMR (CDCl$_3$): δ 7.3, 15.9, 31.5, 84.1, 114.5, 122.4, 129.0, 148.0, 211.6; IR (neat): 3278, 2979, 2937, 1718, 1603, 1495, 1101, 901, 692 cm$^{-1}$; $[\alpha]_D^{23}$ +75.5 (c=0.29, CHCl$_3$); HRMS (FAB): Calculated value [C$_{11}$H$_{15}$NO$_2$]: 193.1103, observed value: 193.1097.

The enantiomeric excess was determined by HPLC using a (Chiralcel) OD-H column (hexane:2-propanol 40:1). 1.0 mL/min; major enantiomer tr=16.5 min, minor enantiomer tr=20.6 min.

Example 25 (Table 6, Entry 6)

Into a CH$_3$CN solution (3.0 mL) of phenylacetoaldehyde (1.8 mmol) and nitrosobenzene (0.6 mmol), super proline (0.06 mmol) is added at 0 deg C., and the solution is stirred for 2 hr at the same temperature. i-PrOH (1.0 mL) and NaBH$_4$ (3 mmol) are added, and stirred for 10 min; then a phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminoxy aldehyde in 50% yield with 99% ee.

The method for determining the optical purity, and the physical values were the same as those in EXAMPLE 13.

Example 26 (Table 6, Entry 7)

Into a CH$_3$CN solution (3.0 mL) of 3-phenyl-propanal (1.8 mmol) and nitrosobenzene (0.6 mmol), super proline (0.06 mmol) is added at 0 deg C., and the solution is stirred for 2 hr at the same temperature. i-PrOH (1.0 mL) and NaBH$_4$ (3 mmol) are added, and stirred for 10 min; then a phosphate buffer solution is added to stop the reaction; organic matters are extracted with ethyl acetate; the organic phase is washed with saline, and dried with Na$_2$SO$_4$. After removing the Na$_2$SO$_4$ by filtration, the solvent is distilled away under reduced pressure. The product is purified by column chromatography to obtain the α-aminoxy aldehyde in 76% yield with 98% ee.

The method for determining the optical purity, and the physical values were the same as those in EXAMPLE 12.

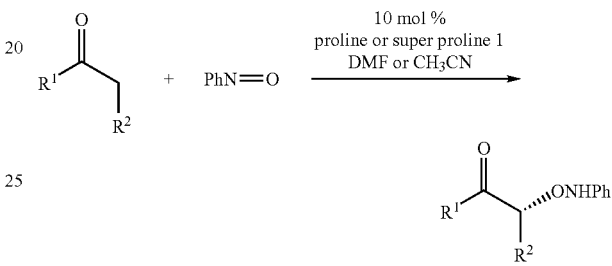

TABLE 6

| Entry | Substrate | Product | Proline Time, hr | Proline yld, % | Proline ee, % | Super proline Time, hr | Super proline yld, % | Super proline ee, % |
|---|---|---|---|---|---|---|---|---|
| 1 | cyclohexanone | cyclohexanone-ONHPh | 5.5 | 77 | >99 | 0.25 | 76 | >99 |
| 2 | 4,4-dimethylcyclohexanone | 4,4-dimethylcyclohexanone-ONHPh | 24 | 84 | >99 | 2 | 74 | >99 |
| 3 | thiopyranone | thiopyranone-ONHPh | 24 | 69 | >99 | 2 | 68 | >99 |
| 4 | cycloheptanone | cycloheptanone-ONHPh | 24 | <5 | nd | 2 | 45 | >99 |

TABLE 6-continued

| Entry | Substrate | Product | Time, hr | Proline yld, % | ee, % | Time, hr | Super proline yld, % | ee, % |
|---|---|---|---|---|---|---|---|---|
| 5 | Et-C(=O)-CH2CH3 (ethyl ketone) | Et-C(=O)-CH(ONHPh)-CH3 | 24 | <5 | nd | 1 | 50 | >99 |
| 6 | H-C(=O)-CH2-Ph | H-C(=O)-CH(ONHPh)-Ph | 24 | <5 | nd | 2 | 50 | 99 |
| 7 | H-C(=O)-CH2-Bn | H-C(=O)-CH(ONHPh)-Bn | 24 | 67 | 98 | 2 | 76 | 98 |

Example 27

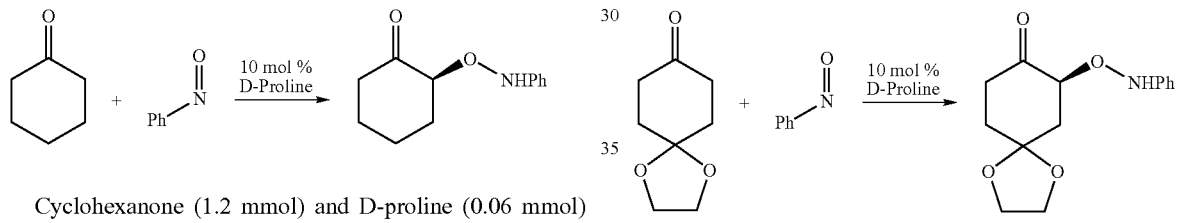

Cyclohexanone (1.2 mmol) and D-proline (0.06 mmol) are dissolved into 2.7 mL of a DMF solution, and the solution is cooled to 0 deg C. Into this solution, a DMF solution (0.9 mL) of nitrosobenzene (0.6 mmol) is dropped over 5.5 hr. After completion of the dropping, the solution is stirred at the same temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the α-aminooxy ketone in 79% yield with ee of >99%.

The optical purity was determined by HPLC using a chiral column.

(S)-2-anilinooxy-cyclohexanone $^1$H NMR ($CDCl_3$): δ 1.37-1.75 (3H, m), 1.82-1.95 (2H, m), 4.27 (2H, dd, J=11.6, 6.2 Hz), 6.82 (3H, t, J=8.1 Hz), 7.12 (2H, t, J=7.6 Hz), 7.71 (1H, s); $^{13}$C NMR ($CDCl_3$): δ 23.6, 27.1, 32.3, 40.7, 86.1, 114.3, 114.8, 128.9, 148.0, 209.7; IR (KBr): 3041, 2942, 2865, 1716, 1600, 1494, 1132, 1099, 1072, 1027 cm$^{-1}$; HRMS (FAB): Calculated value [$C_{12}H_{15}NO_2$]: 205.1103, observed value: 205.1080; $[α]_D^{23}$ −119 (c=0.84, $CHCl_3$).

The enantiomeric excess was determined by HPLC using a Chiralpak AD-H column (hexane:2-propanol 40:1). 1.0 mL/min; major enantiomer tr=28.1 min, minor enantiomer tr=34.3 min.

Example 28

1,4-cyclohexadione monoethyleneketal (1.2 mmol) and D-proline (0.06 mmol) are dissolved into 2.7 mL of a DMF solution, and this solution is cooled to 0 deg C. Into this solution, a DMF solution (0.9 mL) of nitrosobenzene (0.6 mmol) is dropped over 12 hr. After completion of the dropping, the solution is stirred at the same temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the α-aminooxy ketone in 96% yield with ee of >99%.

The optical purity was determined by HPLC using a chiral column.

(S)-7-anilinooxy-1,4-dioxaspiro[4.5]decane-8-on $^1$H NMR ($CDCl_3$): (1.88-2.04 (2H, m), 2.16 (1H, t, J=12.8 Hz), 2.36-2.46 (2H, m), 2.62 (1H, dt, J=14.0, 6.8 Hz), 4.38-4.21 (4H, m), 4.60 (1H, dd, J=12.9, 6.5 Hz), 6.87 (2H, d, J=7.7 Hz), 6.90 (1H, t, J=7.2 Hz), 7.20 (2H, t, J=7.2 Hz); 13C NMR ($CDCl_3$): (34.9, 36.0, 39.7, 64.8, 64.9, 82.7, 107.6, 114.5, 122.2, 128.9, 148.0, 208.6; IR (neat): 2960, 2888, 1728, 1602, 1494, 1305, 1122, 1052 cm$^{-1}$; $[α]_D^{18}$ −78.7 (c=1.2, $CHCl_3$); HRMS (FAB): Calculated value [$C_{14}H_{17}NO_4$]: 263.1158, observed value: 263.1172.

Example 29

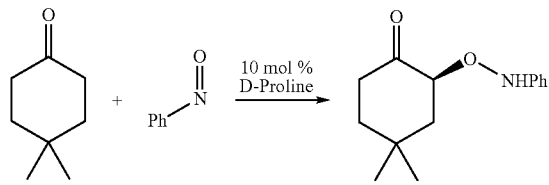

4,4-dimethylcyclohexanone (1.2 mmol) and L-proline (0.06 mmol) are dissolved into 2.7 mL of a DMF solution, and this solution is cooled to 0 deg C. Into this solution, a DMF solution (0.9 mL) of nitrosobenzene (0.6 mmol) is dropped over 12 hr. After completion of the dropping, the solution is stirred at the same temperature for 30 min. A phosphate buffer solution is added to stop the reaction; organic matters are extracted with ethyl acetate; the organic phase is washed with saline, and dried with $Na_2SO_4$. After removing the $Na_2SO_4$ by filtration, the solvent is distilled away under reduced pressure. The product is purified by column chromatography to obtain the α-aminooxy ketone in 87% yield with ee of >99%.

The optical purity was determined by HPLC using a chiral column.

(S)-2-anilinooxy-4,4-dimethylcyclohexanone $^1$H NMR ($CDCl_3$): δ 0.97 (s, 3H), 1.14 (s, 3H), 1.48-1.59 (3H, m), 4.38 (1H, ddd, J=12.7, 6.4, 3.2 Hz), 2.21-2.28 (1H, m), 2.40 (1H, dt, J=14.1, 6.5 Hz), 4.38 (1H, dd, J=12.9, 6.4 Hz), 6.79 (2H, d, J=7.8 Hz), 6.81 (1H, t, J=8.1 Hz), 7.13 (2H, t, J=8.1 Hz); $^{13}$C NMR ($CDCl_3$): δ 24.9, 31.3, 31.9, 44.4, 83.2, 114.2, 121.9, 128.8, 148.1, 210.3; IR (KBr): 3041, 2956, 2927, 1725, 1602, 1495, 1470, 1076, 740, 692 $cm^{-1}$; $[α]_D^{19}$ −85.7 (c=0.33, $CHCl_3$); HRMS (FAB): Calculated value $[C_{14}H_{19}NO_2]$: 233.1416, observed value: 233.1423.

The enantiomeric excess was determined by HPLC using a Chiralcel OD-H column (hexane:2-propanol 40:1). 1.0 mL/min; major enantiomer tr=12.2 min, minor enantiomer tr=9.1 min.

For cyclohexanone, dimethylcyclohexanone, and tetrahydro-4H-thiopyran-4-on, the product was obtained in a period of time much shorter than that when proline is used. For example, for cyclohexanone, the reaction which took 5.5 hr was completed in 15 min. In addition, cycloheptanone and diethylketone reacted slowly with proline, but by using super proline, the α-aminooxy ketones could be synthesized, although the yield was moderate. Any of the compounds obtained has an extremely high asymmetric yield. Because it is already known that the compounds obtained can be induced into the α-hydroxy ketones with a divalent copper salt, (N. Momiyama, H. Yamamoto, J. Am. Chem. Soc., 2003, 125, 6038.), the present reaction can be applied to a method for synthesizing an α-hydroxy ketone having a high optical purity through the asymmetric catalytic reaction from a ketone.

INDUSTRIAL APPLICABILITY

According to the method of the present invention, the corresponding optically active α-aminooxy ketone can be obtained from a ketone and a nitroso compound in a high yield with a high enantioselectivity, using a catalytic amount of proline and, in turn, the α-hydroxy ketone can be effectively obtained.

In other words, the method of the present invention is an advantageous method which eliminates the need for first converting a ketone into an enolate or an equivalent thereof; allows an α-aminooxy ketone derivative to be directly obtained from a ketone; allows use of proline which is low-cost and readily available as an optically active substance; and allows an α-aminooxy ketone derivative having a high yield and a high optical purity to be obtained. When the catalyst is proline, the proline has the feature of being inexpensive. In addition, when the catalyst used is a proline derivative and, in particular, the above-mentioned super proline, the corresponding α-aminooxy ketone can be manufactured simply in a short period of time with a high yield and a high enantioselectivity, as compared to proline.

In addition, the α-aminooxy ketone derivatives obtained can be easily induced into α-hydroxy ketones with a divalent copper salt (Momiyama et al. (Momiyama, N.; Yamamoto, H. J. Am. Chem. Soc., 2003, 125, 6038)), which are useful as medicines and agricultural chemicals.

The invention claimed is:

1. A manufacturing method for an optically active α-aminooxy ketone derivative expressed by formula (1), wherein a ketone expressed by formula (2) is caused to react with a nitroso compound expressed by formula (3) in the presence of proline or a proline derivative expressed by formula (4):

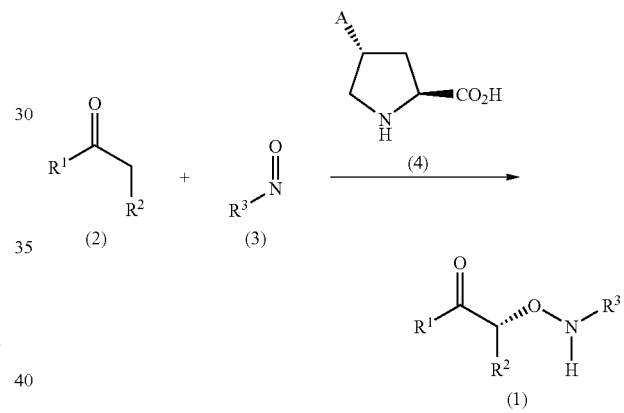

wherein in formulae (1)-(4), $R^1$ and $R^2$ respectively denote an alkyl, alkenyl or alkynyl group which may have a substituent, and $R^1$ and $R^2$ may be linked to form a ring; $R^3$ denotes an aryl, heterocyclic, alkyl, alkenyl or alkynyl group which may have a substituent; and A denotes a hydrocien atom, alkoxy group, aryloxy group, acyloxy group or silyloxy group which may have a substituent, and wherein A in formula (4) is a silyloxy group which may have a substituent.

2. A manufacturing method for an optically active α-aminooxy ketone derivative expressed by formula (1'), wherein a ketone expressed by formula (2) is caused to react with a nitroso compound expressed by formula (3) in the presence of proline or a proline derivative expressed by formula (4'):

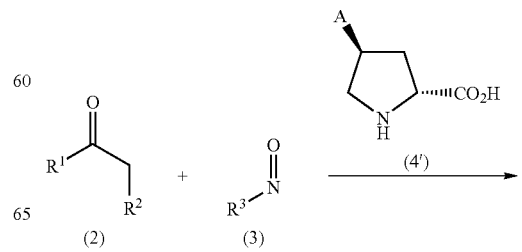

-continued

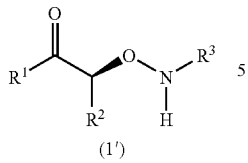
(1')

wherein in formulae (1)-(4), $R^1$ and $R^2$ respectively denote an alkyl, alkenyl or alkynyl group which may have a substituent, and $R^1$ and $R^2$ may be linked to form a ring; $R^3$ denotes an aryl, heterocyclic, alkyl, alkenyl or alkynyl group which may have a substituent; A denotes a hydrogen atom, alkoxy group, aryloxy group, acyloxy group or silyloxy group which may have a substituent and wherein A in formula (4') is a silyloxy group which may have a substituent.

* * * * *